(12) United States Patent
Vardoulis et al.

(10) Patent No.: US 12,196,626 B2
(45) Date of Patent: Jan. 14, 2025

(54) SENSOR APPARATUS FOR NORMAL AND SHEAR FORCE DIFFERENTIATION

(71) Applicant: The Board of Trustees of the Leland Stanford Junior University, Stanford, CA (US)

(72) Inventors: Orestis Vardoulis, Stanford, CA (US); Zhenan Bao, Stanford, CA (US); Clementine M. Boutry, Stanford, CA (US); Marc Negre, Stanford, CA (US); Alex L. Chortos, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 688 days.

(21) Appl. No.: 17/287,824

(22) PCT Filed: Oct. 25, 2019

(86) PCT No.: PCT/US2019/058194
§ 371 (c)(1),
(2) Date: Apr. 22, 2021

(87) PCT Pub. No.: WO2020/087027
PCT Pub. Date: Apr. 30, 2020

(65) Prior Publication Data
US 2021/0396605 A1   Dec. 23, 2021

Related U.S. Application Data

(60) Provisional application No. 62/750,951, filed on Oct. 26, 2018.

(51) Int. Cl.
  *G01L 1/14*   (2006.01)
  *A61B 5/00*   (2006.01)

(52) U.S. Cl.
  CPC .............. *G01L 1/146* (2013.01); *G01L 1/148* (2013.01)

(58) Field of Classification Search
  CPC ... G01L 9/0052; G01L 9/0055; G01L 9/0051; G01L 1/16; G01L 9/0005; G01L 1/142;
  (Continued)

(56) References Cited

U.S. PATENT DOCUMENTS 7,509,869 B2   3/2009   Liu et al.
7,944,008 B2   5/2011   Parks et al.
(Continued)

OTHER PUBLICATIONS

USPTO. International Search Report and Written Opinion dated Feb. 19, 2020, for parent PCT Application No. PCT/US2019/058194, 11 pages.
(Continued)

*Primary Examiner* — Brandi N Hopkins
(74) *Attorney, Agent, or Firm* — Crawford Maunu PLLC

(57) ABSTRACT

Various embodiments are directed to sensor apparatuses and methods thereof. An example sensor apparatus includes a plurality of capacitors and sensor circuitry. The plurality of capacitors including a first substrate having a plurality of first electrodes, a second substrate having a second electrode, and a dielectric material, and with the plurality of first electrodes and the second electrode being separated by the dielectric material. The plurality of first electrodes are aligned with respect to the second electrode such that each of plurality of first electrodes form one of the plurality of capacitors with the second electrode. The sensor circuitry is coupled to the plurality of capacitors to differentiate between normal and shear forces applied to apparatus based on a pattern of impedance responses of each of the plurality of capacitors formed by the second electrode and the plurality of first electrodes.

19 Claims, 28 Drawing Sheets

(58) Field of Classification Search
CPC .. G01L 1/225; G01N 15/0606; G01N 27/127; G01R 15/04; G06F 3/0418; G06F 3/045; G06F 3/0414; G06F 3/0412; G05G 1/38; H01C 10/06
See application file for complete search history.

(56) References Cited

U.S. PATENT DOCUMENTS

| | | | |
|---|---|---|---|
| 9,212,960 | B2 | 12/2015 | Lipomi et al. |
| 9,281,415 | B2 | 3/2016 | Bao et al. |
| 9,347,838 | B2 | 5/2016 | Chen et al. |
| 9,512,545 | B2 | 12/2016 | Zhang et al. |
| 9,625,330 | B2 | 4/2017 | Park et al. |
| 9,841,331 | B2 | 12/2017 | Wood et al. |
| 10,037,098 | B2 * | 7/2018 | Bao ............... G06F 3/04144 |
| 2011/0005325 | A1 * | 1/2011 | Yang ............... H01G 5/16 29/25.41 |
| 2011/0263950 | A1 | 10/2011 | Larson et al. |
| 2012/0119315 | A1 | 5/2012 | Ou et al. |

OTHER PUBLICATIONS

C. M. Boutry et al. A hierarchically patterned, bioinspired e-skin able to detect the direction of applied pressure for robotics. Science Robotics 3, Nov. 21, 2018, 9 pgs. Examiner is respectfully referred to priority U.S. Appl. No. 62/750,951 for source content.
AD7147: CapTouch Programmable Controller for Single-Electrode Capacitance Sensors, Rev. E. Analog Devices, Inc. (2007-2015), 70 pgs. www.analog.com/media/en/technical-documentation/data-sheets/AD7147.
Q. Li, L. Natale, R. Haschke, A. Cherubini, A .- V. Ho, Tactile Sensing for Manipulation, Int. J. Human. Robot, 15(1), 1802001 (2018).
S Haddadin, A De Luca, A Albu-Schaffer, Robot collisions: A survey on detection, isolation, and identification, IEEE Transactions on Robotics 33(6), 1292-312 (2017).
Chortos, A., Liu, J. & Bao, Z. Pursuing prosthetic electronic skin. Nat. Mater. 15, 937-950 (2016).
D. J. Lipomi, et al., Skin-like pressure and strain sensors based on transparent elastic films of carbon nanotubes. Nat. Nanotechnol. 6, 788 (2011).
J. Kim, et al., Stretchable silicon nanoribbon electronics for skin prosthesis. Nature Commun. 5, 5747 (2014).
D. H. Ho, et al., Stretchable and multimodal all graphene electronic skin, Adv. Mater. 28, 2601 (2016).
B. C. K. Tee, C. Wang, R. Allen, Z. Bao, An electrically and mechanically self-healing composite with pressure- and flexion-sensitive properties for electronic skin applications. Nat. Nanotechnol 7, 825 (2012).
S. C. B. Mannsfeld, B. C. K. Tee, R. M. Stoltenberg, C. V. H. H. Chen, S. Barman, et al., Highly sensitive flexible pressure sensors with microstructured rubber dielectric layers, Nature Materials 9, 859 (2010).
Boutry, C. M. et al. A sensitive and biodegradable pressure sensor array for cardiovascular monitoring. Adv. Mater. 27, 6954-6961 (2015).
Boutry, C.M., Kaizawa, Y., Schroeder, B.C et al. A stretchable and biodegradable strain and pressure sensor for orthopaedic application. Nat Electron 1, 314-321 (2018).
J. Park, M. Kim, Y. Lee, H. Sang Lee, H. Ko, Fingertip skin-inspired microstructured ferroelectric skins discriminate static/dynamic pressure and temperature stimuli, Sci. Adv. 1, e1500661 (2015).
S. Yin, V. J. Santos, J. D. Posner, Bioinspired flexible microfluidic shear force sensor, Sensors and Actuators A 264, 289 (2017).
M. H. Lee, H. R. Nicholls, Review Article Tactile sensing for mechatronics-a state of the art survey, Mechatronics 9(1), 1 (1999).
R. S. Dahiya, P. Mittendorfer, M. Valle, G. Cheng, V. J. Lumelsky, Directions toward effective utilization of tactile skin: A review, IEEE Sensors Journal 13(11), 4121 (2013).
H. Yousef, M. Boukallel, K. Althoefer, Tactile sensing for dexterous in-hand manipulation in robotics—A review, Sensors and Actuators A: physical 167(2), 171 (2011).
A. Schmitz, et al., A tactile sensor for the fingertips of the humanoid robot icub, IEEE/RSJ International Conference on Intelligent Robots and Systems (IROS), 11689323, (2010).
Y. Yang, X. Li, X. Zheng, Z. Chen, Q. Zhou, Y. Chen, 3D-Printed Biomimetic Super-Hydrophobic Structure for Microdroplet Manipulation and Oil/Water Separation, Adv. Mater. 30(9), 1704912, (2018).
A. Chortos, G. I. Koleilat, R. Pfattner, D. Kong, P. Lin, R. Nur, et al., Mechanically Durable and Highly Stretchable Transistors Employing Carbon Nanotube Semiconductor and Electrodes., Adv. Mater. 28(22), 4441 (2016).
S. Shang, W. Zeng, X. Tao, High stretchable MWNTs/polyurethane conductive nanocomposites., J. Mater. Chem. 21, 7274 (2011).
A. I. Weber, et al., Spatial and temporal codes mediate the tactile perception of natural textures, Proc. Natl Acad. Sci. USA 110, 17107 (2013).
P. Jenmalm, I. Birznieks, A. W. Goodwin, R. S. Johansson, Influence of object shape on responses of human tactile afferents under conditions characteristic of manipulation, Eur. J. Neurosci. 18, 164 (2003).
V. E. Abraira, D. D. Ginty, The sensory neurons of touch, Neuron 79, 618 (2013).
R. S. Johansson, J. R. Flanagan, Coding and use of tactile signals from the fingertips in object manipulation tasks, Nature Rev. Neurosci. 10, 345 (2009).
B. C.-K. Tee, A. Chortos2, A. Berndt, A. K. Nguyen, A. Tom, A. McGuire, et al., A skin-inspired organic digital mechanoreceptor, Science 350(6258), 313 (2015).
S. Douady, Y. Couder, Phyllotaxis as a physical self-organized growth process, Phys. Rev. Lett. 68(13), 2098 (1992).
C. Nisoli, Spiraling solitons: A continuum model for dynamical phyllotaxis of physical Systems, Phys. Rev. E. 80(2), 026110 (2009).

* cited by examiner

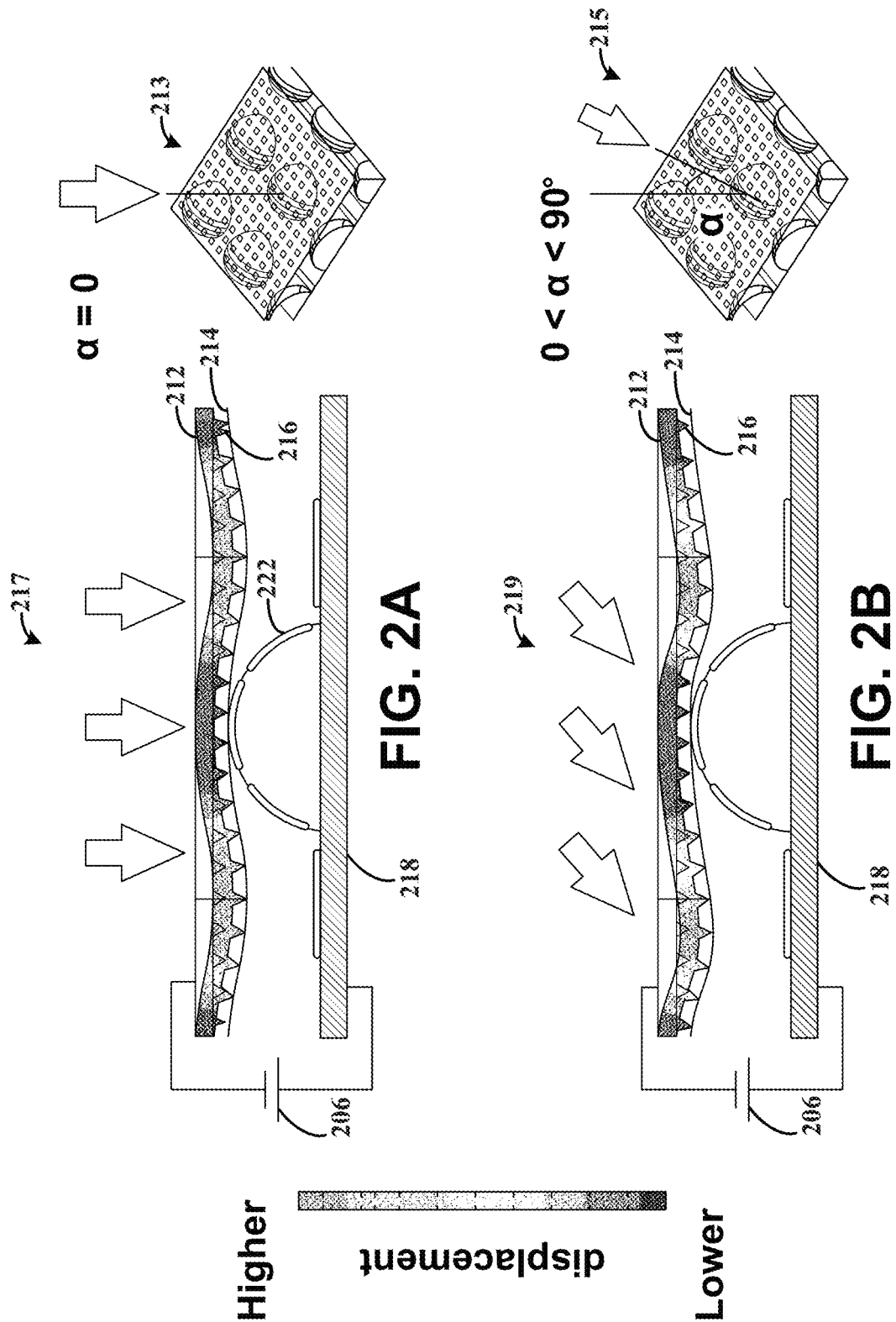

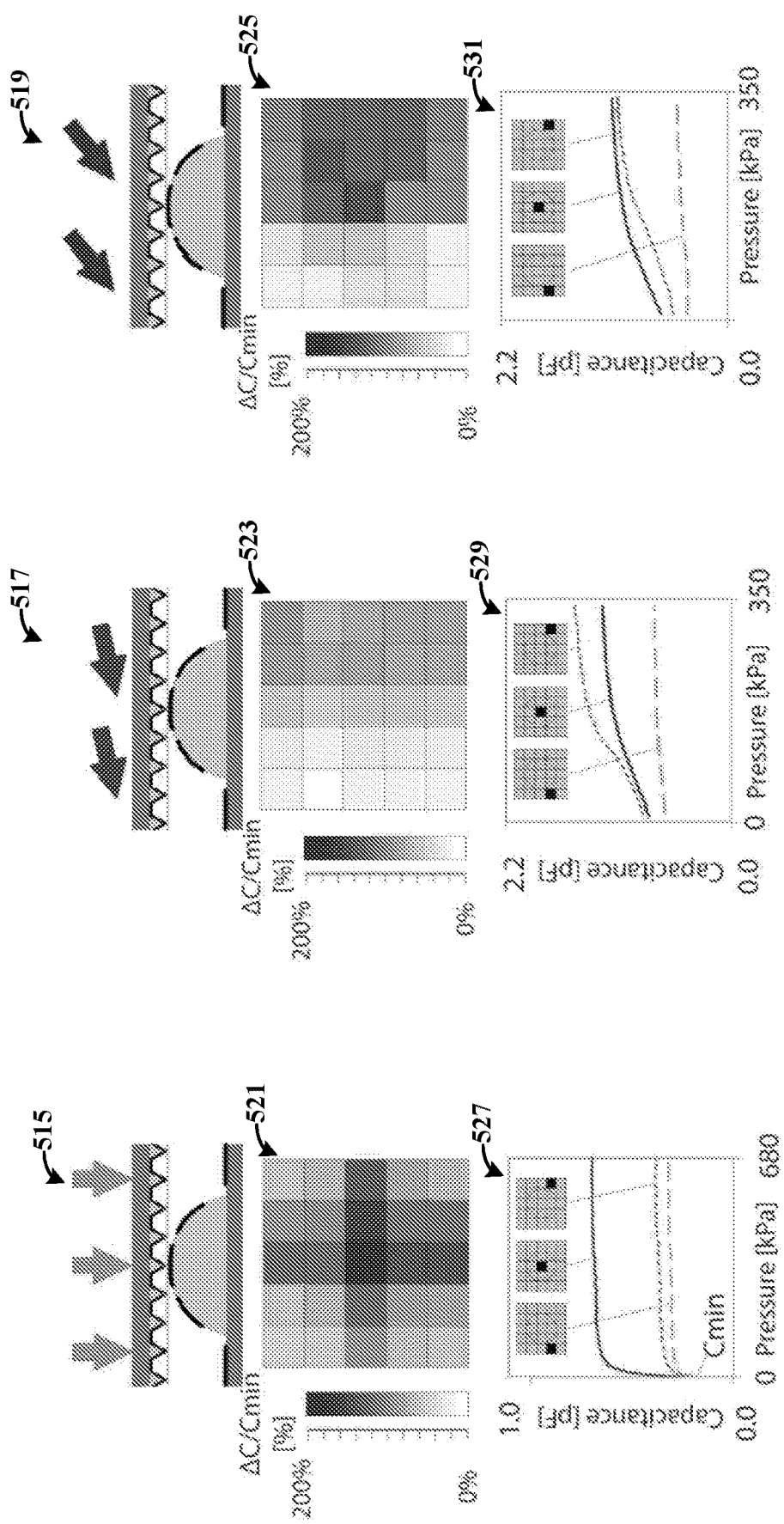

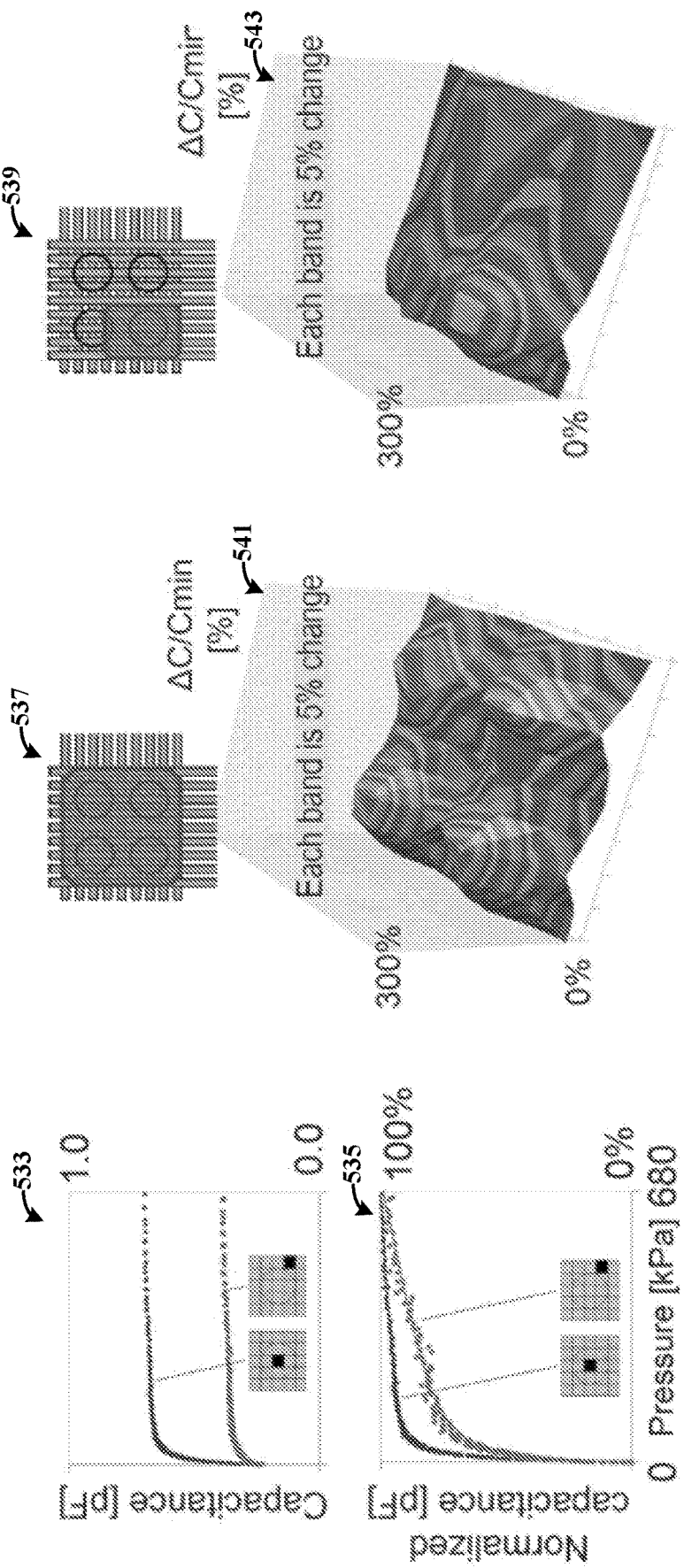

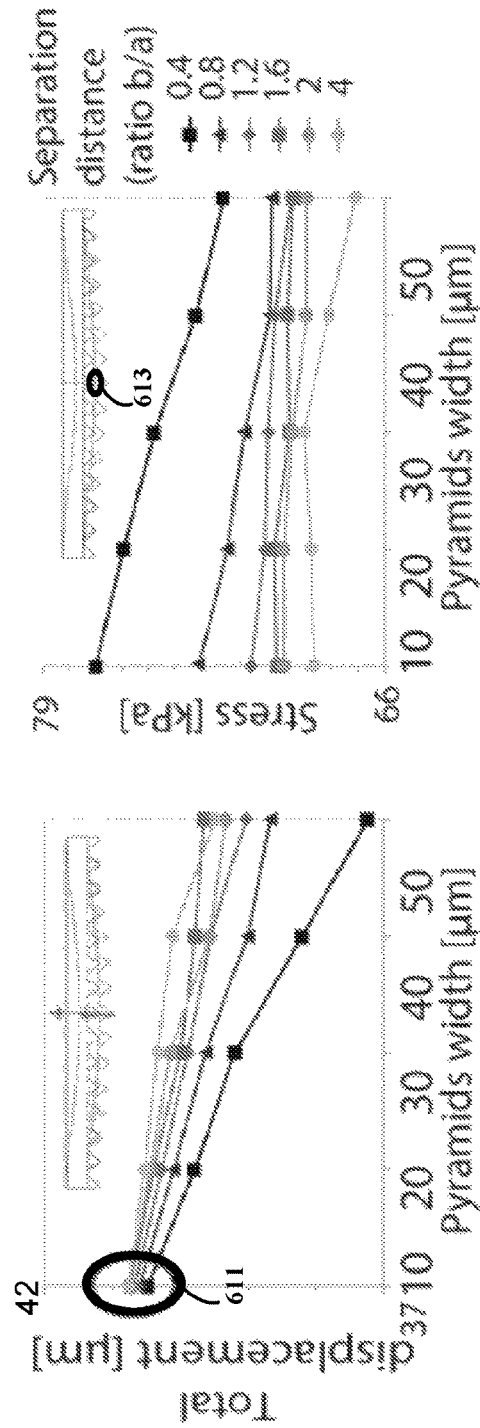
FIG. 6F
FIG. 6G
FIG. 6H

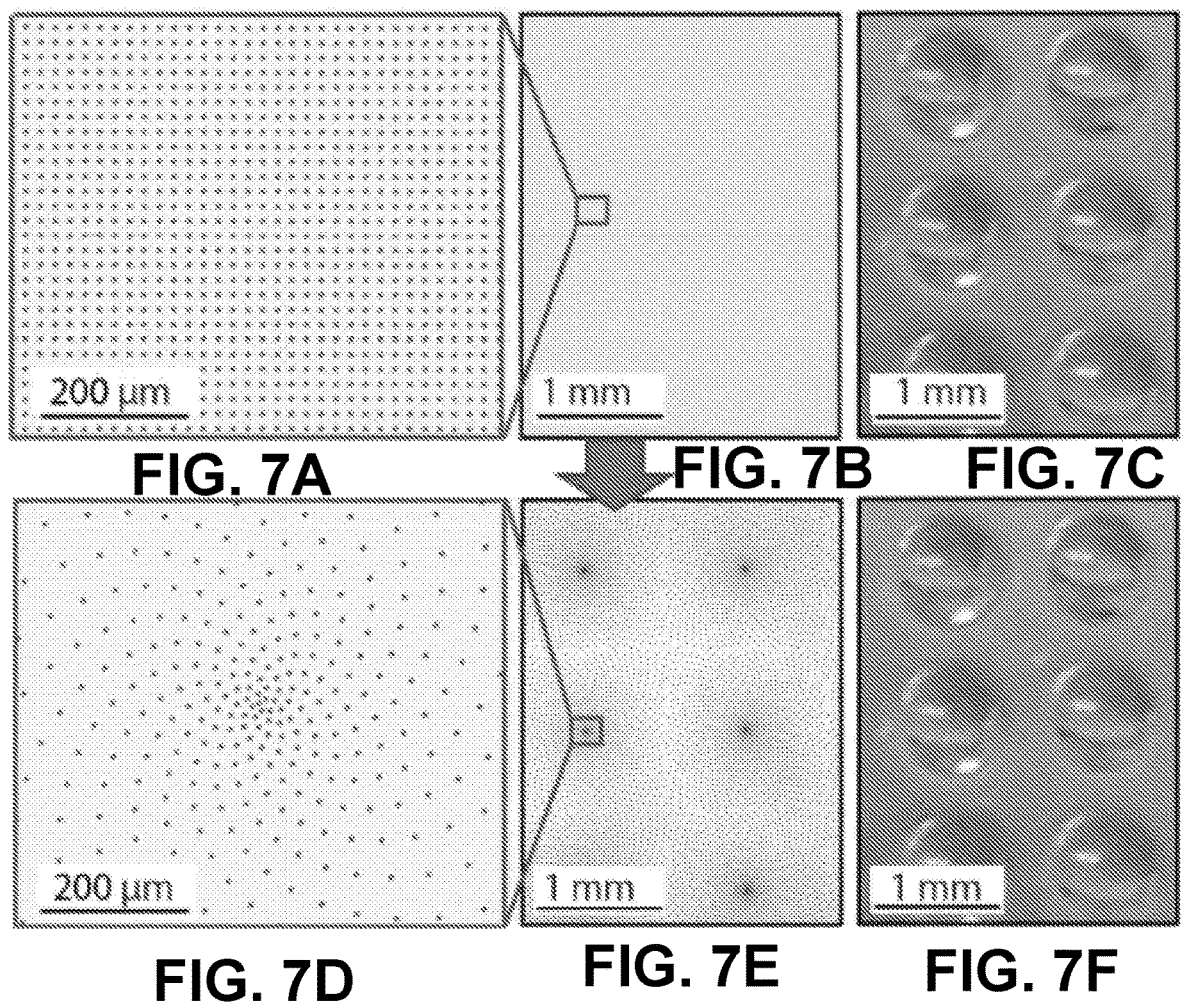

$$C = \varepsilon_r \varepsilon_0 \frac{A}{d}$$

- C  Capacitance
- A  Area of overlap of the two electrodes
- $\varepsilon_r$  Relative static permittivity
- $\varepsilon_0$  Permittivity of vacuum
- d  Separation between the electrodes Separation distance between pyramids b/a = 4

$K1$
$B1$ $$\frac{B1}{K1} \frac{dFk}{dt} + Fk = B1 V(t)$$

$$T = \frac{B1}{K1}$$

b/a = 1.2

$K1...Ki$
$B1...Bi$ $K1=K2=K3$
$B1=B2=B3$ $Keq = K1+K2+K3 = 3K1$
$1/Beq = 1/B1 + 1/B2 + 1/B3$ $$T = \frac{Beq}{Keq} = \frac{1}{9}\frac{B1}{K1}$$

SENSOR APPARATUS FOR NORMAL AND SHEAR FORCE DIFFERENTIATION

Animal skin provides a remarkable network of sensitive diverse sensors that provide sensitive pressure and vibration sensing. Skin can transduce environmental stimuli into physiological signals, which are then interpreted by the brain. Various force sensors and devices may attempt to mimic properties of human or animal skin to provide a variety of features.

Sensors can be used for robotics, such as for surgical robots used in healthcare, domestic robots, and robotic implants (e.g., synthetic appendixes on humans and others). While many advances have been made, domestic robots, such as robotics that perform a variety of functions (e.g., vacuum, clean etc.), are still not a part of everyday life. One reason for this is the lack of dexterous manipulation capabilities for robots, and in particular, the lack of the robotic equivalent to human skin including the ability to perform tactile sensing. Tactile sensing can be used for many types of manipulation tasks in order to provide contact parameters, such as forces, force direction, and location of contact surfaces. In addition, the ability to measure and discriminate between normal and shear forces can be used to provide texture and slippage information. Such parameters may not be obtained using traditional wrist forces, torque and proprioceptive sensors that many robotics use. Furthermore, such parameters can be useful as feedback such as for robotics performing various tasks that may be trivial to a human, e.g., holding a glass of liquid or inserting a key into a lock.

The above issues as well as others have presented challenges to force sensors for a variety of applications.

SUMMARY

Aspects of various embodiments are directed to a sensor apparatus that differentiates between normal and shear forces.

In certain example embodiments, aspects of the present disclosure involve a skin-like sensor apparatus that is sensitive to normal force, shear force, and the combination of both, and can discriminate between the stimuli in real time, such as by discriminating between forces via spatial signal processing of a sensor field grid.

More specific example embodiments are directed to a sensor apparatus that includes a plurality of capacitors and sensor circuitry. The plurality of capacitors including a first substrate having a plurality of first electrodes, a second substrate having a second electrode, and a dielectric material with the plurality of first electrodes and the second electrode being separated by the dielectric material. The plurality of first electrodes are aligned with respect to the second electrode such that each of plurality of first electrodes form one of the plurality of capacitors with the second electrode. The sensor circuitry is coupled to the plurality of capacitors to differentiate between normal and shear forces applied to apparatus based on a pattern of impedance (e.g., capacitance or resistance) responses of the plurality of capacitors formed by the second electrode and the plurality of first electrodes. The sensor circuitry may differentiate between normal, shear, and tilt forces by generating an impedance map that is indicative of the pattern of impedance responses and comparing the impedance map to predetermined patterns.

The first and second electrodes may include three-dimensional microstructures, which are embedded on the first and second substrates, respectively. For example, the plurality of first electrodes include pyramid-shaped microstructures and the second electrode includes a dome-shaped microstructure. The pyramid-shaped microstructures are positioned orthogonally to or in a spiral pattern with respect to the dome-shaped microstructure. The first and second substrates may be formed of an elastomer, such as polyurethane (PU), and/or the plurality of first electrodes and the second electrode are formed of the elastomer and carbon-nanotubes (CNTs). In specific aspects, the second substrate includes a plurality of second electrodes arranged in a pattern. In such aspects, for each of the plurality of second electrodes, a respective subset of the plurality of first electrodes are positioned to align with the respective one of the plurality of second electrodes such that the plurality of first electrodes and plurality of second electrodes form a plurality of arrays of capacitors.

Other specific aspects are directed to a sensor apparatus including a first substrate, a second substrate, and a dielectric material between the first and second substrates. The first substrate has a plurality of pyramid-shaped microstructures and the second substrate has a plurality of dome-shaped microstructures. Each of the plurality of dome-shaped microstructures align with a subset of the plurality of pyramid-shaped microstructures, thereby forming a plurality of arrays of capacitors.

The first and second substrates may be formed of an elastomer material, and the plurality of pyramid-shaped microstructures and dome-shaped microstructures include carbon nanotubes. The elastomer may elastically deform in response to pressure applied, and to store and release energy reversibly. The apparatus may further include sensor circuitry coupled to the plurality of arrays of capacitors and configured and arranged to measure and differentiate between normal and shear forces applied to apparatus based on a pattern of impedance responses of each of the plurality of arrays of capacitors.

In various related aspects, the plurality of pyramid-shaped microstructures and the plurality of dome-shaped microstructures include electrodes, and each array of capacitors includes a plurality of electrode pairs formed by the respective dome-shaped microstructure and the respective subset of pyramid-shaped microstructures of the plurality of pyramid-shaped microstructures.

In specific aspects, each subset of the plurality of pyramid-shaped microstructures is arranged in a phyllotaxis spiral with respect to one of the plurality of dome-shaped microstructures. Additionally and/or alternatively, the plurality of pyramid-shaped microstructures may be arranged in a grid pattern on the first substrate with a distance between of b and having a length of a, wherein the ratio of b/a is from 0.4-4.0. As a further specific aspect, each subset of pyramid-shaped microstructures are arranged with respect to the respective dome-shaped microstructure such that a first pyramid-shaped microstructure of the subset is arranged with respect to a top of the dome-shaped microstructure, four of the pyramid-shaped microstructures of the subset are arranged with respect to slopes of the dome-shaped microstructure, four of the pyramid-shaped microstructures of the subset are arranged with respect to corners of the dome-shaped microstructure, and sixteen of the pyramid-shaped microstructures are arranged surrounding the dome-shaped microstructure.

The sensor apparatus may include an array of capacitors that are formed by top and bottom microstructures embedded in an elastomer material. More specifically, a top elastomer substrate has embedded thereon a plurality of microstructures in a pattern. The plurality of microstructures on the top elastomer substrate can be three-dimensional structures, such as pyramid-shaped structures. The bottom elastomer substrate additionally has embedded thereon a plurality of microstructures in a pattern. The plurality of microstructures on the bottom elastomer substrate can be three-dimensional structures, such as dome-shaped structures. The microstructures may be formed of the elastomer, such as the PU elastomer, and have carbon-nanotubes coated thereon. The pattern of microstructures on the top and bottom elastomer substrates can be positioned orthogonally to one another, such that a subset of the three-dimensional structures on the top elastomer substrate respectively form a capacitor with a dome-shaped structure on the bottom elastomer substrate. In other embodiments, the pattern of microstructures on the top elastomer substrate are positioned in a spiral pattern with respect to the microstructures on the bottom elastomer substrate. In specific embodiments, the microstructures on the top and bottom elastomer substrates includes CNTs, elastomer, and/or rubber based structures.

In specific embodiments, the top substrate includes a two-dimensional array of molded square pyramids, which may be formed of CNTs or rubber. These microstructures allow the elastomer to elastically deform when an external pressure is applied, storing and releasing energy reversibly, thus minimizing undesirable viscoelastic behavior and resulting in enhanced sensitivity. The bottom elastomer substrate includes a two-dimensional array of molded domes (e.g., hill-like structures), which provide for measuring and discriminating the direction of the applied force. The elastomer is flexible and durable, and allows for the transfer of CNTs thereon. The combination of microstructures-elastomer based electrodes can provide for superior electrical stability, even with applied mechanical deformation.

In a number of related aspects, the sensor circuitry includes at least one capacitance-to-digital converter circuitry that connects the electrodes to an input channel of the capacitance-to-digital converter circuitry. The sensor circuitry can measure capacitance at a sampling rate using the capacitance-to-digital converter circuitry and connected processing circuitry. Additionally and/or alternatively, the apparatus includes one or more additional electrodes used as a part of a transducer circuit and further including a passively or inductively powered circuit configured to provide power to at least the sensor circuitry. The apparatus, in specific aspects, includes wireless communication circuit for wirelessly communicating signals from the sensor circuitry.

Other example aspects are directed to a method of forming the above-described sensor apparatus. The method may include forming a first substrate of elastomer having a plurality of pyramid-shaped microstructures embedded thereon, and forming a second substrate of elastomer having a plurality of dome-shaped microstructures embedded thereon. The example method further includes combining the first substrate and the second substrate, with a dielectric substrate between, such each one of the plurality of dome-shaped microstructures is aligned with a different subset of plurality of pyramid-shaped microstructures, and the plurality of pyramid-shaped microstructures and dome-shaped microstructures form a plurality of arrays of capacitors. For example, the aligned first substrate, dielectric substrate and second substrate may be laminated together.

In specific aspects, forming the first substrate may include patterning a silicon wafer with pyramid shapes, coating the silicon wafer with a CNT material, forming an elastomer substrate on the wafer with the CNT material adhering, and releasing the elastomer substrate from the wafer to form the first substrate having the plurality of pyramid-shaped microstructures embedded thereon. Forming the second substrate may include patterning a silicon wafer, coating the silicon wafer with a CNT material, forming an elastomer substrate on the wafer with the CNT material adhering, releasing the elastomer substrate from the wafer to form the second substrate, applying a vacuum to the second substrate to form the plurality of dome-shaped microstructures embedded thereon.

In various specific aspects, the above-described sensor apparatus is formed as part of another apparatus, such as a robotic or prosthetic apparatus. As a specific example, the sensor apparatus can be part of a robotic hand. When applied in a robotic hand, the sensor apparatus can be used to detect slip of an object being held or touched by the robotic hand. In related specific aspects, the sensor apparatus is formed as part of another apparatus having a plurality of different types of sensors including the sensor circuitry, pressure sensor circuitry, strain sensor circuitry, and/or temperature sensor circuitry, among other types of sensors. The apparatus can further include a wireless communication circuit for wirelessly communicating signals from the sensor circuitry. In some related aspects, the apparatus includes one or more of the electrodes used as a part of a transducer circuit and further including a passively or inductively powered circuit configured to provide power to at least the sensor circuitry of the apparatus. The apparatus can further include a computer (e.g., CPU and/or microcontroller) to provide or assess the forces based on signals provided from the sensor circuitry.

The above discussion/summary is not intended to describe each embodiment or every implementation of the present disclosure. The figures and detailed description (and referring to the underlying Provisional Application fully incorporated herein) that follow also exemplify various embodiments.

BRIEF DESCRIPTION OF FIGURES

Various example embodiments may be more completely understood in consideration of the following detailed description in connection with the accompanying drawings, in which:

FIGS. 2A-2C show an example sensor apparatus under different forces and patterns of the respective microstructures, consistent with embodiments of the present disclosure;

FIGS. 5A-5I show an example sensor apparatus under different forces and resulting capacitive patterns, consistent with embodiments of the present disclosure;

FIGS. 6A-6H show an example of a sensor apparatus under different forces, consistent with embodiments of the present disclosure;

FIGS. 7A-7G show example microstructure patterns, consistent with embodiments of the present disclosure;

Figure 1A:
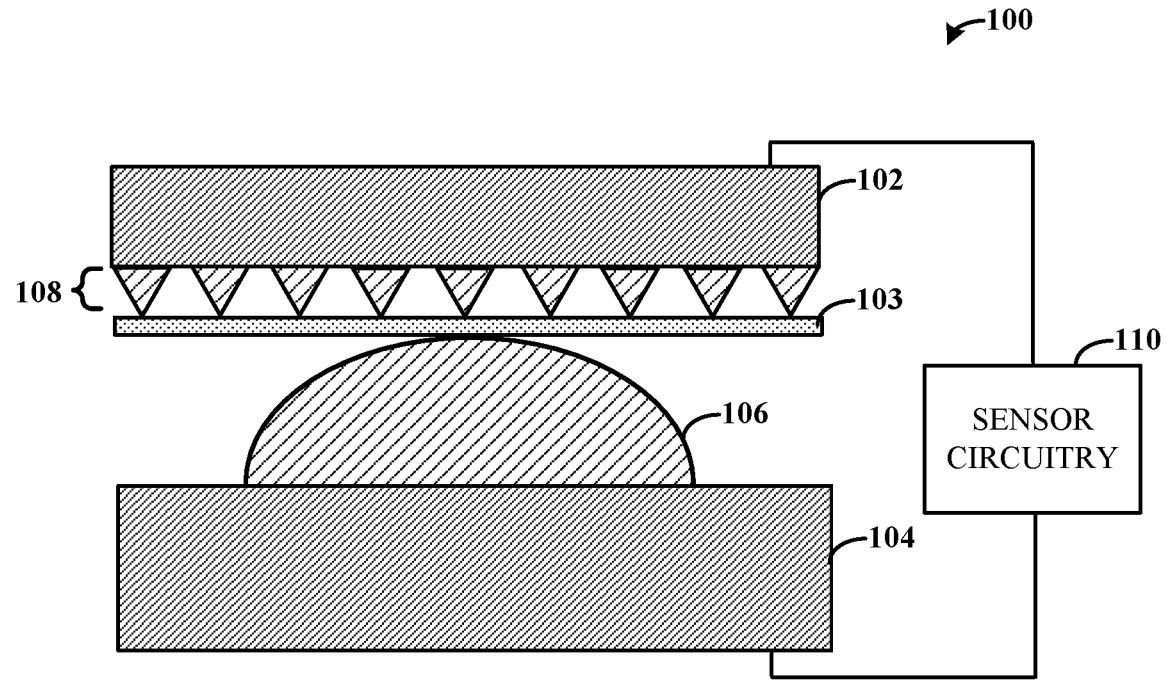
FIGS. 1A-1B show example sensor apparatuses, consistent with embodiments of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are applicable to a variety of different types of apparatuses and methods involving a sensor apparatus that senses forces applied thereto and that defines both the magnitude and type of the force. In certain implementations, aspects of the present disclosure have been shown to be beneficial when used in the context of a skin-like tactile sensor for robotic or prosthetic application, such as robotic hands, but it will be appreciated that the instant disclosure is not necessarily so limited. Various aspects may be appreciated through the following discussion of non-limiting examples which use exemplary contexts.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element. Also, although aspects and features may in some cases be described in individual figures, it will be appreciated that features from one figure or embodiment can be combined with features of another figure or embodiment even though the combination is not explicitly shown or explicitly described as a combination.

Embodiments of the instant disclosure are directed to methods and apparatuses (e.g., systems, devices and circuitry) configured for providing tactile sensing by measuring and discriminating between normal and shear forces. Tactile sensing can be used for a variety of purposes, such as for dexterous manipulation of objects in robotics. Distinguishing between such forces in real time can be beneficial for slip detection and interaction with fragile objects. Embodiments in accordance with the present disclosure include a sensor apparatus that uses impedance-based sensing to measure and discriminate between normal and shear forces in real time. The sensor apparatus includes an array of capacitors formed by top and bottom electrodes, such as carbon nanotubes (CNTs)-based electrodes. The sensing ability is provided by a three-dimensional structure that can mimic the interlocked dermis-epidermis interface in human skin. For example, the top electrode can include pyramid-shaped CNT microstructures arranged along phyllotaxis spirals, with one spiral per dome-shaped CNT microstructure of the bottom electrode, and that results in a skin-like sensor apparatus with increased sensitivity, minimal hysteresis, excellent cycling stability and response time in the millisecond range. In specific embodiments, the skin-like sensor apparatus can be used to control a robot arm for a variety of tasks and/or provide tactile feedback, although embodiments are not limited to robotics and the sensor apparatus can be used for a variety of purposes.

In accordance with a number of embodiments, the array of capacitors is formed by a first substrate and a second substrate. The first substrate and second substrate are formed of an elastomer material and have embedded thereon a plurality of microstructures. The plurality of microstructures of the first elastomer substrate are formed in a pattern and can include three-dimensional shapes, such as pyramid-shaped microstructures. The plurality of microstructures of the second elastomer substrate are formed in a pattern and can include three-dimensional shapes, such as dome-shaped microstructures. The dome-shaped microstructures can be hill-like, such as semi-spheres, and/or semi-spheroids. An intermediate substrate or material of dielectric is formed between the first and second elastomer substrates, with the respective microstructures positioned to contact the dielectric material. The dielectric material provides electrical insulation of the capacitors. In specific embodiments, the microstructures are formed using CNTs, and can be referred to as CNT microstructures, although embodiments are not so limited and the microstructures can be formed using a variety of material, such as rubber and/or of both rubber and CNTs.

The patterns of microstructures on the top and bottom elastomer substrates can be positioned orthogonally to one another, such that a subset of the three-dimensional structures on the top elastomer substrate respectively form an array of capacitors with a dome-shaped structure on the bottom elastomer substrate. For example, the first and second substrates with microstructures are aligned perpendicular to one another such that each dome-shaped microstructure on the second elastomer substrate corresponds or otherwise aligns with a subset of the plurality of pyramid-shaped microstructures. In specific embodiments, each dome-shaped microstructure corresponds with twenty-five pyramid-shaped microstructures (one on top of the dome, four on the slopes of the dome, four on the corners of the dome, and sixteen surrounding the dome) forming the array of capacitors, sometimes referred to as a "sensor array", although embodiments are not so limited and the subset may include sixteen or nine pyramids per dome. Such alignment results in the pyramid-shaped microstructures being positioned according to a grid, such as a phyllotaxis spiral grids with one spiral per dome.

Figure 1B:
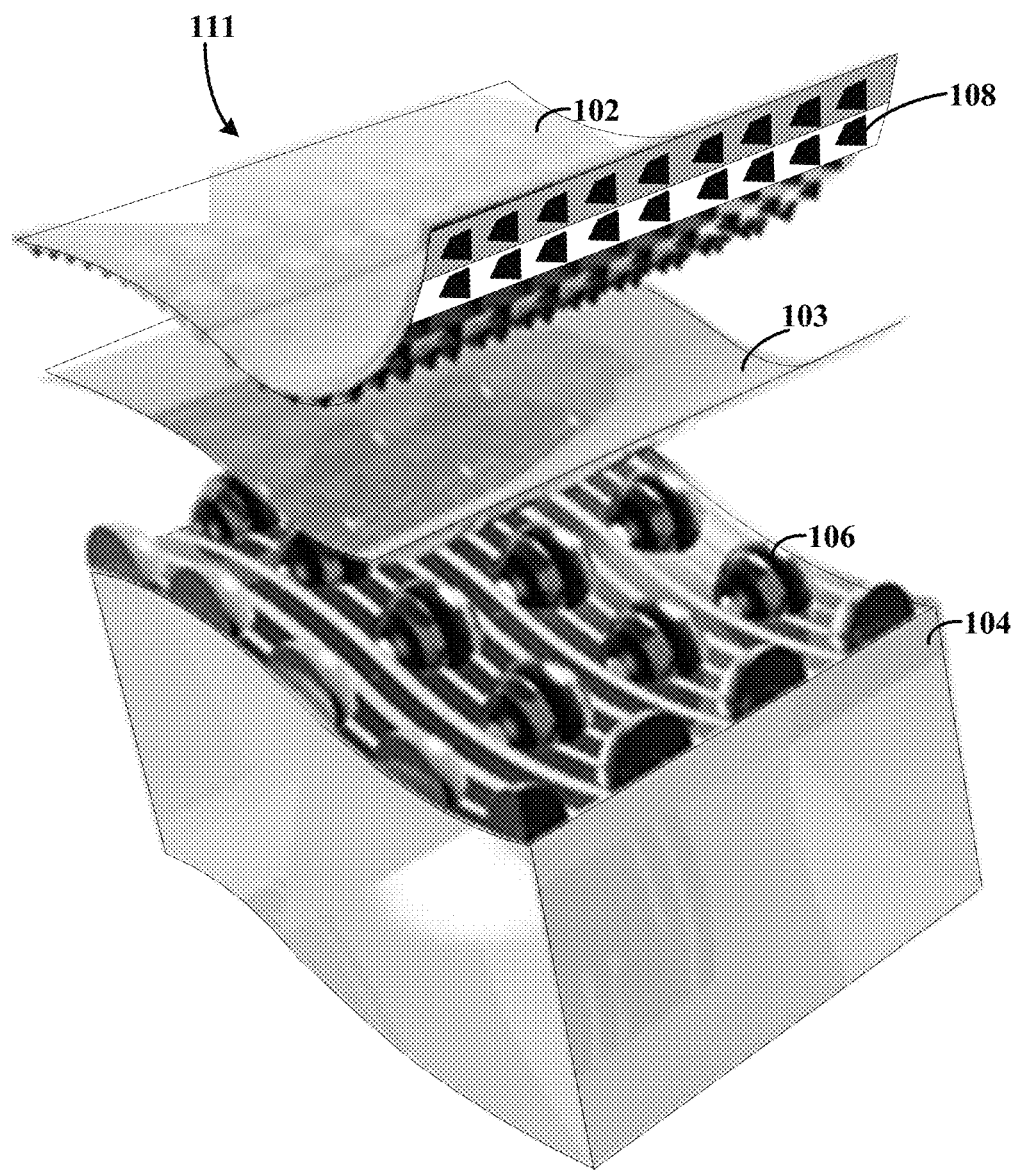

Turning now to the figures, FIGS. 1A-1B show example sensor apparatuses, consistent with embodiments of the present disclosure. The sensor apparatus 100 include a plurality of capacitors coupled to sensor circuitry 110 and used to detect both the type and magnitude of force applied is flexible for application on surfaces that are not smooth.

As shown by FIG. 1A, the sensor apparatus 100 includes a plurality of capacitors formed of at least two substrates 102, 104. The substrates 102, 104 each include at least one electrode 108, 106 and are separated from one another by a dielectric substrate or material 103. In specific embodiments, the substrates 102, 104 are formed of a flexible elastomer material and the electrodes 106, 108 can be formed on or embedded with the flexible substrates. The first substrate 102 can include a plurality of first electrodes 108 and the second substrate 104 can include one or more second electrodes 106 (e.g., such as illustrated by FIG. 1B) forming a plurality of electrode pairs.

The dielectric substrate or material 103 and the substrates 102, 104 can include a structure formed of a stretchable elastomer, such as Polydimethylsiloxane (PDMS), Polyurethane (PU), poly(styrene-butadiene-styrene) (SBS), styrene butylene styrene (SEBS), poly(vinylidene fluoride-co-hexafluoropropylene) (PVDF-HFP), although embodiments are not so limited.

The plurality of first electrodes 108 of the first substrate 102 may be aligned with the second electrode 106 of the second substrate such that each of plurality of first electrodes 108 form one of the plurality of capacitors with the second electrode 106. The second electrode 106 thereby forms a plurality of capacitors with the plurality of first electrodes 108, which is sometimes interchangeably herein referred to as "an array of capacitors" or "a sensor array". The plurality of first electrodes 108 and/or the second electrode 106 may be formed of an elastomer material and/or CNTs. For example, the first and second substrates 102, 104 are formed of PU and the respective electrodes 106, 108 are embedded thereon and formed of PU with a coating of CNTs, although embodiments are not so limited.

The plurality of first electrodes 108 include three-dimensional microstructures embedded on the first substrate 102 and the second electrode 106 includes a three-dimensional microstructure embedded on the second substrate 104. As used herein, a microstructure includes or refers to a structure formed of a physical material that has one or more dimensions in the micron range. In various embodiments, the plurality of first electrodes 108 each include pyramid-shaped microstructures and the second electrode 106 includes a dome-shaped microstructure. The pyramid-shapes may include a triangular pyramid, a square or rectangular pyramid, a pentagonal pyramid, among others. A dome-shape may include or be hill-like, such semi-spheres, and/or semi-spheroids. Each of the electrodes 106, 108 may be solid or may be hollow. In some embodiments, the pyramid-shaped microstructures are positioned orthogonally with respect to the dome-shaped microstructure. In other embodiments, the pyramid-shaped microstructures are positioned in a spiral pattern with respect to the dome-shaped microstructure.

The sensor apparatus 100 further includes sensor circuitry 110 coupled to the plurality of capacitors formed by the first and second substrates 102, 104. The sensor circuitry 110 may be used to detect the magnitude and direction of a force, such as a randomly-combined force including normal, shear, and rotation forces with high sensitivity and sensing range. In various specific embodiments, the sensor apparatus 100 is used to measure a capacitive transduction system that takes advantage of the unique geometry of capacitive electrodes, e.g., the different shaped microstructures of the first substrate 102 and the second substrate 104.

More specifically, the sensor circuitry 110 differentiates between normal and shear forces applied to the sensor apparatus 100 based on a pattern of impedance responses of each of the plurality of capacitors formed by the second electrode 106 and the plurality of first electrodes 108. The pattern of impedance (e.g., capacitance or resistance) responses may include or be used to generate an impedance map indicative of the impedance changes of different electrode pairs of the plurality of capacitors. The impedance map may include pixels or boxes that provide an indication of the impedance response of a respective electrode pair. In specific examples, the impedance map includes a grid of pixels. For example, the sensor circuitry 110 is to differentiate between normal, shear, and tilt forces by generating the impedance map that is indicative of the pattern of impedance responses and comparing the impedance map to predetermined patterns.

The sensor circuitry 110 may include at least one capacitance-to-digital converter (CDC) circuitry that connects the electrodes to an input channel of the CDC circuitry. The sensor circuitry 110 can measure capacitance at a sampling rate using the CDC circuitry and connected processing circuitry, such as a controller. To measure dynamic force by such a sampling rate, the sensor uses two CDC circuitry (Capacitance-to-Digital Converter chips) to connect the electrode pairs to 2 of the 12 analog input channels of each chip, since a high sampling rate (>500 Hz) can be obtained from a lower number of capacitor inputs to the chip. The CDC chip consists of a sigma-delta-based CDC with 12 analog input channels and communicates with a microcontroller via an I2C bus, measuring capacitance in 0.3-1.2 kHz sampling rate, and cancelling noise from capacitors through active shield function. For more information on CDC chips and active shield function, reference is made to AD7147, Analog, http://www.analog.com/media/en/technical-documentation/data-sheets/AD7147.pdf, which is fully incorporated herein by reference.

Additionally and/or alternatively, the apparatus 100 includes one or more additional electrodes used as a part of a transducer circuit and further including a passively or inductively powered circuit configured to provide power to at least the sensor circuitry 110. The apparatus 100, in specific aspects, includes a wireless communication circuit for wirelessly communicating signals from the sensor circuitry. The sensor circuitry 110 and/or the apparatus 100 further include a power circuit to provide an electric potential across the terminals of the plurality of capacitors. Alternatively and/or in addition, the apparatus 100 can further include a computer (e.g., CPU and/or microcontroller) to provide or assess the forces based on signals provided from the sensor circuitry.

Although only one second electrode 106 is illustrated, embodiments are not so limited and the second substrate 104 may include a plurality of second electrodes arranged in a pattern. In such embodiments, for each of the plurality of second electrodes, a respective subset of the plurality of first electrodes 108 of the first substrate 102 are positioned to align with the respective one of the plurality of second electrodes such that the plurality of first electrodes and plurality of second electrodes form a plurality of arrays of capacitors.

FIG. 1B illustrates a specific example sensor apparatus, which is consistent with the sensor apparatus of FIG. 1A. The sensor apparatus 111 has first and second substrates 102, 104 that each include a plurality of electrodes and are separated from one another by a dielectric substrate or material 103.

The electrodes of the first substrate 102 include pyramid-shaped microstructures and the electrodes of the second substrate 104 include dome-shaped microstructures, as respectively illustrated by the particular pyramid-shaped microstructure 108 and the dome-shaped microstructure 106. Each of the plurality of dome-shaped microstructures align with a subset of the plurality of pyramid-shaped microstructures, thereby forming a plurality of arrays of capacitors. Each array of capacitors includes a plurality of electrode pairs formed by the respective dome-shaped microstructure and the respective subset of pyramid-shaped microstructures of the plurality of pyramid-shaped microstructures. The subset of pyramid-shaped microstructures may be aligned to effectively surround or center the respective dome-shaped microstructure.

The first and second substrates 102, 104 may be formed of an elastomer material, such as PU. The pyramid-shaped microstructures and dome-shaped microstructures may include CNTs coated on the elastomer. For example, the structures are formed of PU elastomer and coated with CNTs. The elastomer may elastically deform in response to pressure applied thereto, and may store and release energy reversibly. The dielectric substrate or material 103 may be thinner than the first and second substrates 102, 104 and provides electrical insulation to the capacitors. In a further specific embodiment, the plurality of pyramid-shaped microstructures are arranged in a grid pattern on the first substrate with a distance between of b and having a length of a, wherein the ratio of b/a is from 0.4-4.0.

The pyramid-shaped microstructures and dome-shaped microstructures (e.g., the top and bottom electrodes) may be aligned. For example, respective subsets of the pyramid-shaped microstructures are aligned with each of the dome-shaped microstructures. In specific examples, the pyramid-shaped microstructures are aligned perpendicularly with each of the dome-shaped microstructures aligned perpendicularly, such that an array of capacitors is formed. Sensor apparatuses having a plurality of dome-shaped microstructures may include a plurality of array of capacitors, which each array being associated with one of the plurality of dome-shaped microstructures.

In specific embodiments, the first substrate 102 has twenty-five pyramid-shaped microstructures of the first substrate 102 for each of the one dome-shaped microstructures of the second substrate 104, such that there are twenty-five electrode pairs, or twenty five capacitors, per dome-shaped microstructure of the second substrate 104. In such embodiments, each subset includes twenty-five pyramid-shaped microstructures associated with one of the plurality of dome-shaped microstructures, resulting in the twenty five electrode pairs per dome. As a specific example, each subset of pyramid-shaped microstructures are arranged with respect to the respective dome-shaped microstructure such that a first pyramid-shaped microstructure of the subset is arranged with respect to a top of the dome-shaped microstructure, four of the pyramid-shaped microstructures of the subset are arranged with respect to slopes of the dome-shaped microstructure, four of the pyramid-shaped microstructures of the subset are arranged with respect to corners of the dome-shaped microstructure, and sixteen of the pyramid-shaped microstructures are arranged surrounding the dome-shaped microstructure.

The impedance may be measured between each of the pyramid shaped-microstructures or electrodes at the first substrate 102 and the corresponding dome-shaped microstructure or electrode of the second substrate 104 and across the dielectric substrate or material 103. The electrodes store electric charges which leads to change in impedance. An intermediate dielectric substrate or material 103 provides separation and electrical insulation of capacitors and is polarized by an applied electric field on the electrode layers. The microstructures allow the elastomer to elastically deform when an external pressure is applied, storing and releasing the energy reversibly, thus minimizing undesirable viscoelastic behavior and resulting in enhanced sensitivity.

Although not illustrated by FIG. 1B, the sensor apparatus 111 may further include sensor circuitry coupled to the plurality of arrays of capacitors and configured and arranged to measure and differentiate between normal and shear forces applied to apparatus based on a pattern of impedance responses of each of the plurality of arrays of capacitors. Sensor circuitry, in accordance with the present disclosure, can discriminate forces with a spatial signal processing on the grid at each time step, so that the controller's bandwidth (therefore the performance) can be higher.

Figure 2C:
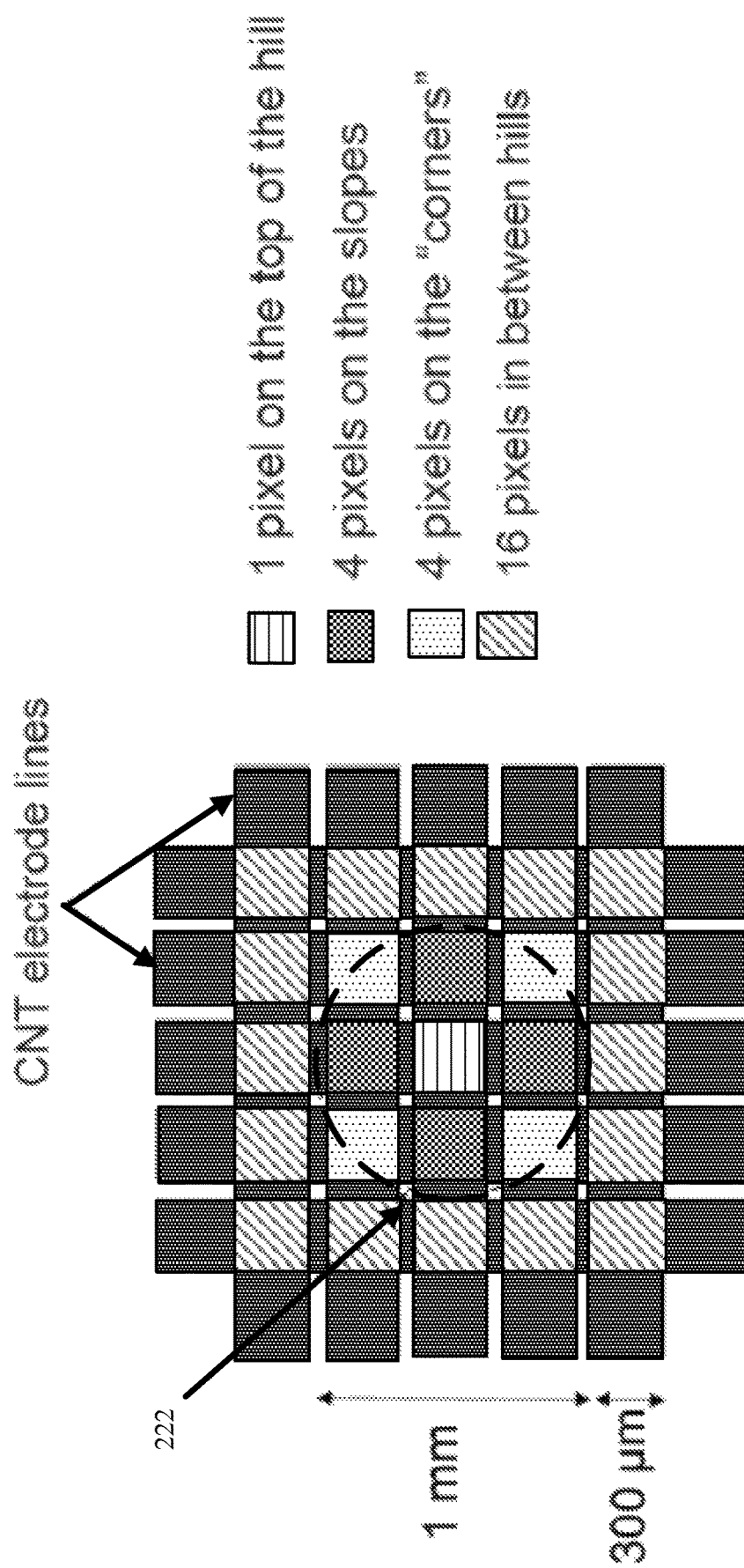

FIGS. 2A-2C show an example sensor apparatus under different forces and patterns of the respective microstructures, consistent with embodiments of the present disclosure. More specifically, FIGS. 2A and 2B illustrate the first and second substrates 212, 218 having an array of capacitors as illustrated by the top down views 213, 215 of the apparatus. For example, subsets of the microstructures of the first substrate 212 form a plurality of capacitors with a respective one of the microstructures of the second substrate 218. The first and second substrates 212, 218 are separated by a dielectric substrate 214. FIGS. 2A-2B show additional side views 217, 219 of one of the dome-shape structures 222 of the second substrate 218 and the subset of pyramid-shapes microstructures (as illustrated by one of the pyramid-shaped microstructures 216) of the second substrate 218 with different types of forces applied to the first substrate 212 and which cause different impedance patterns. As shown, the first substrate 212 flexes in response to the force applied, and the dome-shaped microstructures cause different changes in impedance for respective electrode pairs and which depend on the type of force. The distinction between the different forces can be based on the shape of the impedance response curve as a function of time that differs from one mechanical stimulus to the other. As shown by FIGS. 2A-2B, a power source 206 may be coupled to the terminals of the capacitors, as previously described.

FIG. 2C illustrates an example pattern of the pyramid-shaped electrodes as aligned with a dome-shaped electrode to form a plurality of capacitors. For example, FIG. 2C can include a top-down view of the first and second substrate of FIGS. 2A-2B.

The forces may be distinguished based on patterns of impedance response of the electrode pairs using coupled sensor circuitry. The pattern of impedance responses can be represented as a map, with a pixel representing an impedance value between the dome-shaped microstructure and one of the pyramid-shaped microstructures.

As previously described, the magnitude of normal and shear static forces can be measured by measuring, monitoring and/or analyzing changes in impedance derived from changes in distances between respective electrode pairs (e.g., the gap distance) and changes in overlapping areas of the electrode pairs, respectively. The normal and shear forces can be distinguished based on the comparison of impedance from each electrode pairs of one (or more) arrays of capacitors of the apparatus. As used herein, normal forces includes or refers to pressure or compression forces on the sensor circuitry. Shear forces includes or refers to unaligned forces pushing in different directions. Tilt includes or refers to the combination of normal and shear forces.

Figure 3A:
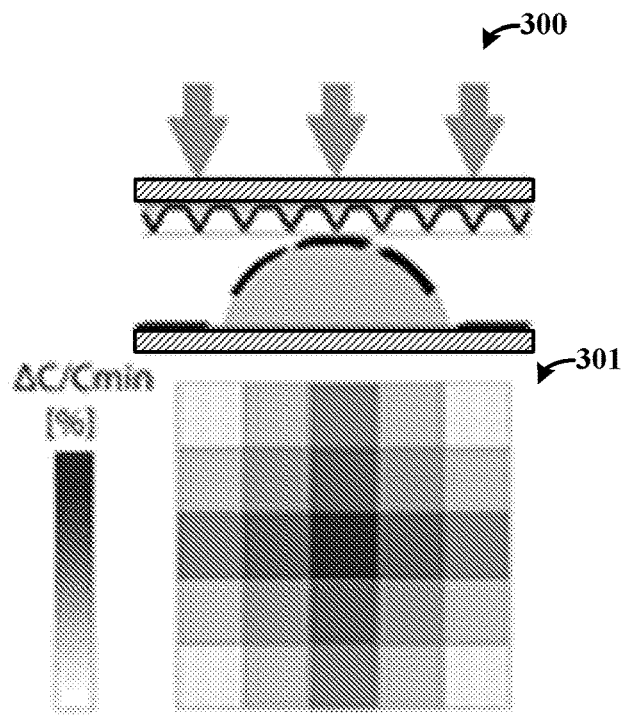
FIGS. 3A-3C show an example sensor apparatus under different forces, consistent with embodiments of the present disclosure.
Figure 3B:
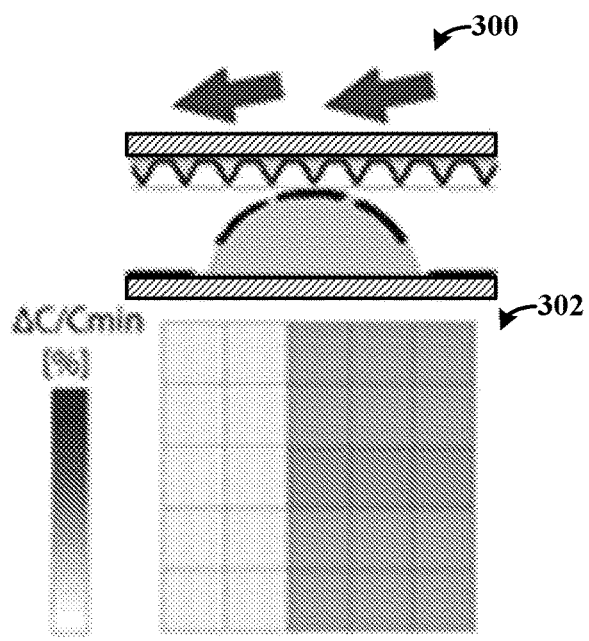
Figure 3C:
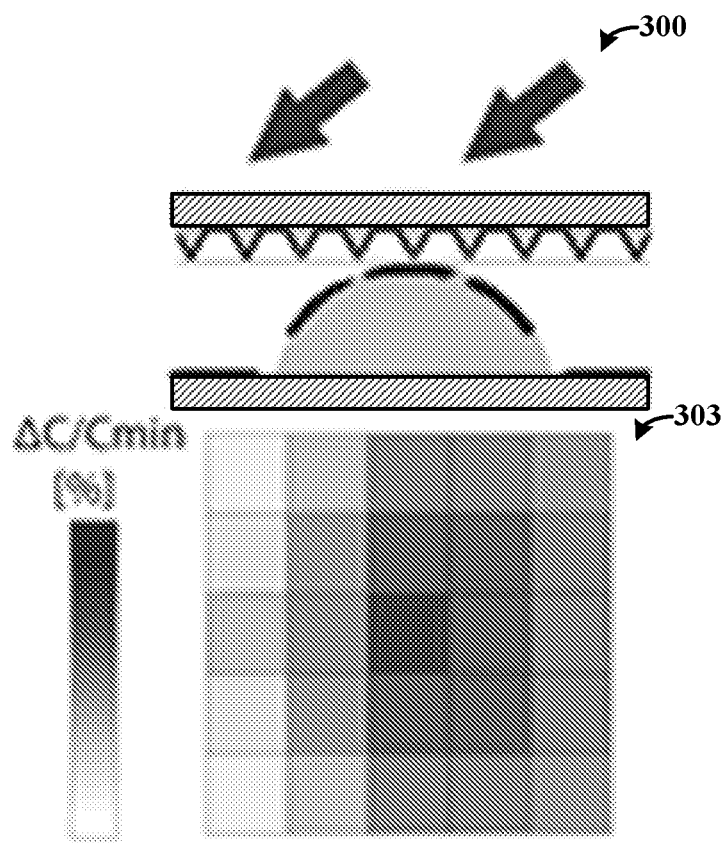

FIGS. 3A-3C show an example sensor apparatus under different forces, consistent with embodiments of the present disclosure. More specifically, FIG. 3A shows a resulting pattern of impedance responses to a normal force applied to the first and second substrate of the sensor apparatus 300, as is consistent with FIG. 2A. FIGS. 3B-3C show resulting patterns of impedance responses to a shear force and tilt forces applied to the first and second substrate of the sensor apparatus 300, as is consistent with FIG. 2A. As may be appreciated, a tilt force may include a combination of normal and shear forces.

The patterns of impedance responses may change depending on both the type of force, the direction of the force, and the amount of force applied. The distinction between the different forces can be based on the shape of the response curve as a function of time and that differs from one mechanical stimulus to the other. Shown by FIGS. 3A-3C, the pattern of capacitive responses of the electrode pairs may include or be generated as an impedance map 301, 302, 303 having pixels, with each pixel (e.g., box) representing one of the electrode pairs associated with a dome-shaped microstructure of the apparatus 300. In the specific example, an array of capacitors associated with one of dome-shaped microstructure of the apparatus 300 includes an array of 5×5 sensing pixels represented in a grid. An intensity of the impedance value is presented by each sensing pixel. The impedance maps 301, 302, 303 show different patterns for different forces. For example, the impedance map 301 of FIG. 3A illustrates an example response to a normal force, the impedance map 302 of FIG. 3B illustrates an example response to a shear force, and the impedance map 303 of FIG. 3C illustrates an example response to a tilt force, all forces being applied to the apparatus 300.

Although various embodiments are described as including twenty-five electrode pairs represented by 5×5 pixels, examples are not so limited and may include different numbers of electrode pairs and/or pixel representations. For example, in the case of a robotic application, the data of a fraction of the twenty-five pixels can provide sufficient information (for instance, nine of them, one on the top of the dome/hill, four on the sides, and four in the corners). For example, embodiments may include sixteen electrode pairs represented by 4×4 pixels and/or nine electrode pairs represented by 3×3 pixels.

Figure 4A:
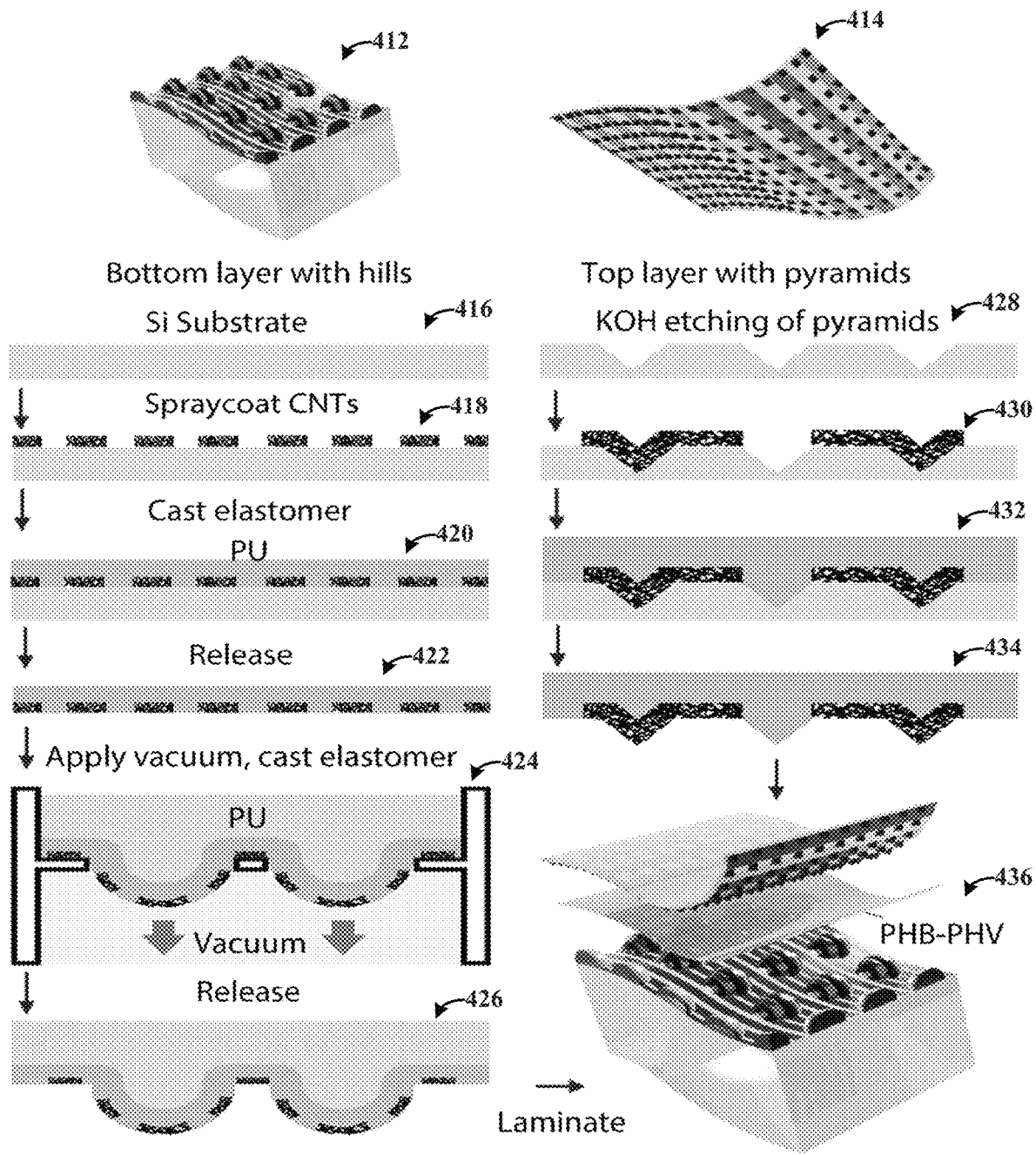
FIGS. 4A-4B show an example of fabricating a sensor apparatus, consistent with embodiments of the present disclosure.
Figure 4B:
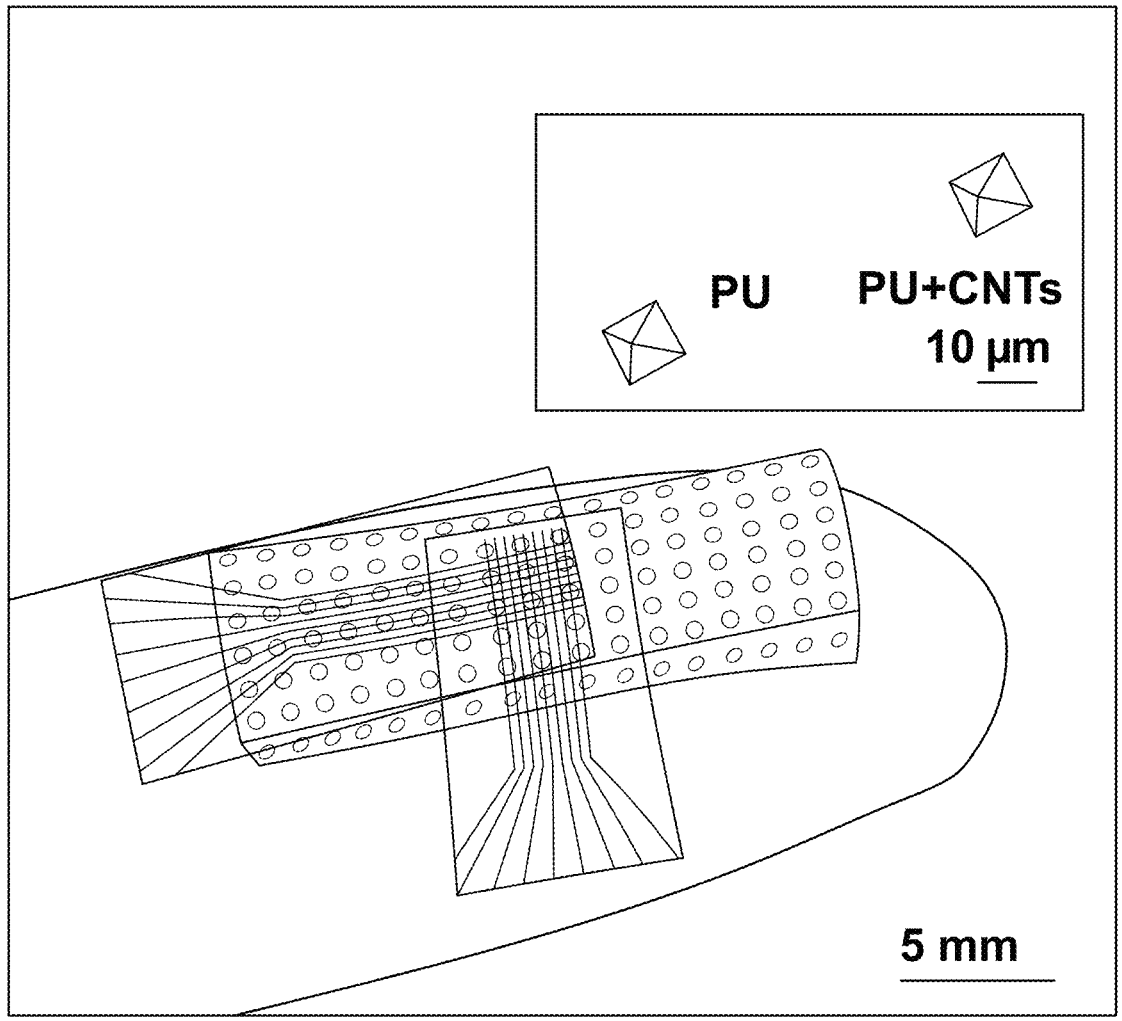

FIGS. 4A-4B show an example of fabricating a sensor apparatus, consistent with embodiments of the present disclosure. The assembly of the sensor apparatus may involve a benchtop process involving the lamination of the bottom electrode layer with the dome-shaped microstructures, the intermediate dielectric layer, and the top electrode layer with pyramid-shaped microstructures.

The fabrication process for the sensor apparatus can include electrode formation, dielectric layer formation, and bonding. The fabrication processing can include forming (e.g., printing) electrode pairs on one or more flexible substrates, building a dielectric layer on a first (or more) of the flexible substrates, bonding the dielectric layer of the first flexible substrate to a second flexible substrate. To print electrode patterns on flexible substrates, photolithography, laser ablation, inkjet printing or three-dimensional (3D) printing can be employed on flexible substrate. To build dielectric layers on these patterned electrodes, a dielectric structure is made with various methods; such as photolithography, laser ablation, laser additive, inkjet printing, 3D printing, dissolvable material frame, emulsion droplet frame to sponge frame technique. This solidified dielectric structure can bond to a patterned electrode by chemical bond (e.g., chemical glue). Further, the dielectric layer bonded to the electrode is bonded to another electrode by plasma treatment and, optionally, the process may be repeated to stack two electrode pairs. In various specific embodiments, the fabrication process can automate alignment of electrode pairs within the sensor circuitry.

More specifically, FIG. 4A illustrates an example method which includes forming a first substrate 414 of elastomer having a plurality of pyramid-shaped microstructures embedded thereon. Forming the first substrate may include patterning a silicon wafer with pyramid shapes (e.g., patterned with pyramids of different sizes by lithography followed by HF oxide etching and finally an anisotropic potassium hydroxide (KOH) etching, at 428. The silicon wafer may be coated with a CNT layer, at 430. After the coating, the first elastomer substrate is formed (e.g., casted) on the wafer with the carbon-nanotube adhering to the elastomer, at 432. The first elastomer substrate may then be released from the wafer to form the first substrate 414 having the plurality of pyramid-shaped microstructures embedded thereon, at 434.

The method further includes forming a second substrate 412 of elastomer having a plurality of dome-shaped microstructures embedded thereon. For example, a silicon wafer is patterned, at 416, and then coated with a CNT layer, at 418, which may include a pattern of CNTs (e.g., not continuous). After the coating, the second elastomer substrate is formed (e.g., casted) on the wafer with the carbon-nanotube adhering to the elastomer, at 420, and the second elastomer substrate with the CNT layer may then be released from the wafer to form the second substrate, at 422. The dome-shapes may be generated on the elastomer substrate using a vacuum process. For example, a vacuum is applied and released to the second substrate 412 to form the plurality of dome-shaped microstructures embedded thereon the second substrate which are proximal to the CNT layer, at 424 and 426.

The method further includes combining the first substrate 414 and the second substrate 412, with a dielectric substrate between, at 436, such that each one of the plurality of dome-shaped microstructures is aligned with a different subset of plurality of pyramid-shaped microstructures, and the plurality of pyramid-shaped microstructures and dome-shaped microstructures form a plurality of arrays of capacitors. For example, the dielectric substrate may be bonded to one of the first and second substrates, and then the second and first substrate are bonded together. The method may include laminating the aligned first substrate, dielectric substrate and second substrate.

The second substrate 412 may be thicker than the first substrate 414, and the dielectric substrate may be thinner than both the first and second substrates 412, 414. As an example, the first substrate 414 may include a PU material having a thickness in the μm range (such as 60 μm-thick) and has the array of pyramid-shaped microstructures. The second substrate 412 may include a PU material that has a thickness in the mm range (such as 1 mm-thick) with an array of dome-shaped microstructures. The domes may have a diameter in the mm range and a height in the μm, such as a diameter of 1 mm and height of 200 μm. The dielectric material may have a thickness in the μm range, such as 10 μm thick. In specific embodiments, the dielectric substrate or material is polyhydroxybutyrate/polyhydroxyvalerate (PHB/PHV) and used as a spacer between the first and second substrates 412, 414. The electrodes are made of spray-coated and photolithography-patterned conducting CNTs embedded into the PU matrix (electrodes width 300 μm, separation distance between two electrodes 50 μm). The construct may reinforced with tape at the sides, to mitigate or prevent sliding of the substrate layers when shear force is applied. If the sensor array is scaled, proper adhesion between layers can be implemented to ensure mechanical stability. For example sensor sizes, tape is sufficient to stabilize the system for lab experiments.

FIG. 4B illustrates an optical image showing the CNTs-PU interconnects for signal recording LCR (inductancecapacitance-resistance) meter and scanning electron microscopy (SEM) image of the top e-skin layer with molded pyramids, showing CNTs-PU and PU areas (inset).

The above described fabrication process may be scaled readily, and results in a geometrical configuration with several benefits. The resulting sensor apparatus presents a high density of mechanoreceptor-like sensors. Each dome corresponds to twenty-five capacitors each 90,000 µm² in size (e.g., one capacitor at the top of the dome, four on the slopes, four on the corners of the dome and sixteen surrounding the dome), and the location of each sensing pixel is controlled and ensured by proper alignment. As may be appreciated, embodiments are not limited to twenty-five capacitors per dome and may include other numbers such as sixteen and nine.

In accordance with various embodiments, the proposed design has the ability to detect the direction of applied force. Because of the 3D geometry of the domes/hills and the anisotropic deformation of the top layer with applied tilt force, the capacitors located on the side of the dome are exposed to a greater pressure can have a larger increase in impedance than those located on the other side opposite to the applied force direction.

The sensor circuitry can measure dynamic force by using the same transduction technology used for the static force by applying a high sampling rate (>500 Hz). As previously described, to measure dynamic force by such a sampling rate, the sensor uses two CDC chips to connect the two electrode pairs to two of the twelve analog input channels of each chip.

In some specific embodiments, the sensor apparatus is formed of a flexible metalized mylar, hundreds nm-thick conductive material is ablated or printed on top of a micron-thick flexible film, including Polyethylene terephthalate (PET), Polylmide Kapton (PI), and ITO film, and a stretchable elastomer having the apertures. The elastomer may be Polydimethylsiloxane (PDMS), Polyurethane (PU), poly(styrene-butadiene-styrene) (SBS), styrene butylene styrene (SEBS), poly(vinylidene fluoride-co-hexafluoropropylene) (PVDF-HFP), among other elastomers. These materials are selected by considering mechanical and electrical properties of the target application. The electrode material is flexible and the dielectric material is flexible and stretchable, such that the resulting sensor is responsive to multi-axis force. Higher dielectric elastomer is also expected to be more sensitive.

Sensor apparatuses in accordance with the present disclosure may have a variety of dimensions. For example, the first substrate with the first electrodes or the pyramid-shaped microstructures may have a thickness in a range of 0.1 nanometer (um) to several centimeters (cm) (e.g., a thickness not less than about 0.1 um and not more than several cm, such as 2 cm, 3 cm, 4 cm, 10 cm and more). The second substrate having a second electrode or a plurality of second electrodes/the dome-shaped microstructures may have a thickness in a range of 0.1 um to several cm, and which in specific embodiments includes a range of 0.1 um and 3 cm or 4 cm (e.g., a thickness of not less than about 0.1 um and not more than several cm). The dielectric material may have a thickness in a range of 0.1 um to several millimeters (mm) (e.g., a thickness of not less than about 0.1 um and not more than several mm or less in other embodiments), with the thickness of the dielectric material impacting the impedance measured. In a specific example, the dielectric material is 10 um thick and the second substrate is 3 mm thick, although embodiments are not so limited. The total thickness of the first substrate, the second substrate and the dielectric material may be in a range of 50 um to several cm, and in some specific examples, 100 um to 10 cm or to 200 cm (e.g., a thickness of not less than about 50 um and not more than several cm). The first electrodes or pyramid-shaped microstructures may have a (pyramid) width in a range of 1 um to several hundreds of um, a (pyramid) height in a range of 1 um to several hundreds of um, and a distance between respective pyramids (e.g., two consecutive pyramids) in a range of 1 um and several hundreds of um, and in more specific embodiments in a range of 3 um and 900 um or about 999 um. For example, the pyramid-shaped microstructures may exhibit a width of not less than about 1 um and not more than about several hundreds of um, a height of not less than about 1 um and not more than about several hundreds of um, and a distance between of not less than about 1 um and not more than several hundreds of um. The second electrode(s) or dome-shaped microstructures may have a (dome) diameter in a range of 2 um to several cm, and a (dome) height of 2 um to about half of the diameter (or one half of several cm). In a specific embodiment, the domes have a diameter of around 800 um with a height of a 200-900 hundred um. For example, the dome-shaped microstructures may exhibit a diameter of not less than 2 um and not more than several cm, and in some specific embodiments, not less than 3 um and not more than 6 um. The dome-shaped microstructures may exhibit a height of not less than 2 um and not more than 5 cm, and in specific embodiments not less than 2 um and not more than 3 um.

As used herein, several includes or refers to 2 or more, such as 2-4, 2-5 2-6, 2-7, 2-9, 2-10, 2-15, 2-25, 2-50, 2-90, 2-99, and 2-100 in various examples. For example, several hundreds may include 200-700, 200-900, 200-999, and 2-1000, among other ranges. Similarly, several cm, mm, and/or um may include 2-4, 2-5, 2-6, 2-7, 2-9, 2-10, 2-15, 2-25, 2-50, 2-90, 2-99, and 2-100, among other ranges. Although embodiments are not limited to the above dimension ranges, and sensor apparatuses may be formed in a variety of dimensions for different applications.

Various specific embodiments can include integrating the above-described sensor apparatus with robotics and prosthetics. For example, the sensor apparatus can be applied on target surfaces of robots for a robotic tactile sensing system as the mechanoreceptors of robot skin. On the robot skin or other prosthetic, a flexible three-axis capacitive tactile sensor is freely applicable and indispensable for three distinct kinds of dexterous activities: response, manipulation, and exploration; which include the activity of response of detection and reaction to external agents, manipulation of contact location and force control, and exploration of surface texture and local features. In specific implementations, the sensor circuitry is formed as part of a robotic hand and is used to detect slip of an object being held or touched by the robotic hand. In related specific aspects, the sensor circuitry is formed as part of an apparatus (e.g., robotics, prosthetics and other implementations) having a plurality of different types of sensors including the sensor circuitry, pressure sensor circuitry, strain sensor circuitry, and/or temperature sensor circuitry, among other types of sensors.

Embodiments in accordance with the present disclosure are not limited to a sensor circuitry that is placed on an exterior surface (e.g., proximal to the environment) of robotics or prosthetics apparatus and can be directed to implants or other applications. In some specific embodiments, the sensor circuitry and/or an apparatus including the sensor circuitry can be implanted under an external surface of the skin of a user or other animal, e.g., is subdermal, and/or below a surface of the robotics or prosthetic, similar to or including a passive radio frequency (RF) pet implant. For example, the sensor circuitry can be implanted at a depth below the surface of the skin sufficient to be subcutaneous but not in muscle (e.g., within interstitial space of a user or other animal and/or prosthetic) and/or below a surface or the exterior surface of the robotics/prosthetic. In various embodiments, the implant is located below the surface of the skin, robotic and/or prosthetic sufficient for the implant including the sensor circuitry to communicate with external circuitry (e.g., to receive and output communications such as RF or other wireless signals).

Experimental/More Detailed Embodiments

In various embodiments, the above-described sensor apparatuses may be used for robotic type applications. Tactile sensing can be used for the dexterous manipulation of objects in robotic applications. In particular, the ability to measure and distinguish, in real time, between normal and shear forces is useful for slip detection and interaction with fragile objects. Embodiments in accordance with the present disclosure are directed to a biomimetic soft electronic skin composed of an array of capacitors, capable of measuring and discriminating in real time both normal and tangential forces. The electronic skin (e-skin) apparatus can include a 3D structure that mimics the interlocked dermis/epidermis interface in human skin. Moreover, pyramid microstructures arranged along phyllotaxis spirals result in an e-skin with increased sensitivity, minimal hysteresis, excellent cycling stability and response time in the millisecond range. The e-skin is used to control a robot arm in various tasks, illustrating its potential application in robotics with tactile feedback. Such an e-skin can use multiple levels of biologically inspired patterning, capable of discriminating both normal and tangential forces. The following more detailed/experimental embodiments describes an e-skin formed by layers of elastomer (e.g., PU) material having CNT microstructures thereon, however embodiments are not limited to such material.

FIGS. 5A-5I show an example sensor apparatus under different forces and resulting capacitive patterns, consistent with embodiments of the present disclosure. The sensor apparatus may be consistent with that described by FIGS. 1A-1B and 3A-3C and has a first substrate with a plurality of pyramid-shaped microstructures, a second substrate with a plurality of dome-shaped microstructures and a dielectric substrate between. Each of the dome-shape microstructures pair with a subset of the plurality of pyramid-shaped microstructures.

FIGS. 5A-5C illustrate the different patterns of impedance responses to normal force (FIG. 5A), shear force (FIG. 5B) and tilt force (FIG. 5C). The impedance pattern, which is illustrated as the impedance map 521, 523, 525 indicative of impedance values of electrode pairs associated with a dome, provides the ability to differentiate several types of applied forces, while an individual pixel alone is not able to provide this information. The impedance maps include pixels (e.g., the boxes) associated with each electrode pair formed by one of the subset of pyramid-shaped microstructures and the respective dome-shaped microstructure. In the specific example, a 5×5 sensor array is associated with each dome, however examples are not so limited. The impedance values of the 5×5 capacitors, centered around the dome, are characterized by measuring the pressure response curve upon applied normal force.

FIG. 5A illustrates a cross-sectional view 515 of at least a portion of an apparatus that includes a subset of pyramid-shaped microstructures centered around one dome-shaped microstructure and with normal force applied, as illustrated by the arrows. The relative change in impedance, such as changes in capacitance ($\Delta C/C_{min}=(C_{700\ kPa}-C_{min})/C_{min}$, where $C_{min}$ and $C_{700\ kPa}$ are the capacitances without and with applied pressure, respectively) is shown for the twenty-five capacitors, as shown by the impedance map 521. The measured pressure response curves are shown by the graph 527 for three capacitors (e.g., one located at the top of the dome/hill and two located at the bottom, surrounding the dome/hill). The circle represents the location of the dome-shaped microstructure. The normal force may be applied and measured multiple times.

FIG. 5B illustrates a cross-sectional view 517 of the at least portion of the apparatus, as illustrated by FIG. 5A, and with shear force applied and which may include a normal force of 5-10 kPa, the shear force being illustrated by the arrows. The relative change in impedance ($\Delta C/C_{min}$ with $\Delta C=(C_{340\ kPa}-C_{min})$) is shown for the twenty-five capacitors, as shown by the impedance map 523. The patterns for normal and shear forces are distinct, as shown by FIGS. 5A and 5B. The measured pressure response curves are shown by the graph 529 for three capacitors at different locations. The circle represents the location of the dome-shaped microstructure. The normal force may be applied and measured multiple times.

FIG. 5C illustrates a cross-sectional view 519 of the at least portion of the apparatus, as illustrated by FIG. 5A, and tilt force applied, the tilt force being illustrated by the arrows. The relative change in impedance ($\Delta C/C_{min}$ with $\Delta C=(C_{340\ kPa}-C_{min})$) is shown for the twenty-five capacitors, as shown by the impedance map 525. The pattern for the tilt force includes a combination of the pattern for normal and shear forces, as shown by FIGS. 5A-5C. The measured pressure response curves are shown by the graph 531 for three capacitors at different locations. The circle represents the location of the dome-shaped microstructure. The normal force may be applied and measured multiple times.

FIG. 5D illustrates example impedance graphs 533, 535. The capacitors of the array have a different pressure response curves (and sensitivity) depending on their location. The first graph 533 illustrates capacitive response characteristics, for applied normal force, for two capacitors located at the top and at the bottom of the dome-shaped microstructure, respectively. The second graph 535 illustrates normalized response curves for the two capacitors. The slopes are used to calculate the sensitivities in various pressure ranges.

Figure 11B:
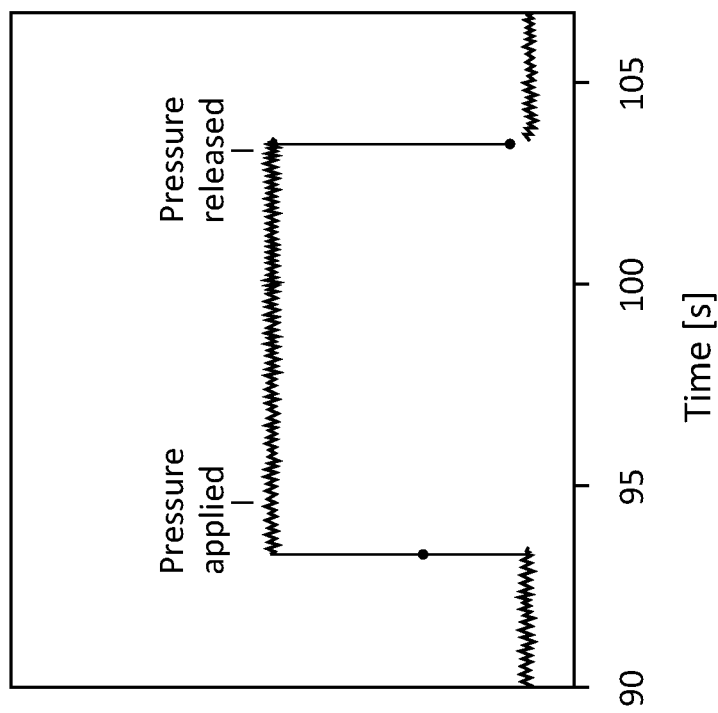
FIGS. 11A-11D shows example performance of a sensor apparatus, consistent with embodiments of the present disclosure.
Figure 11A:
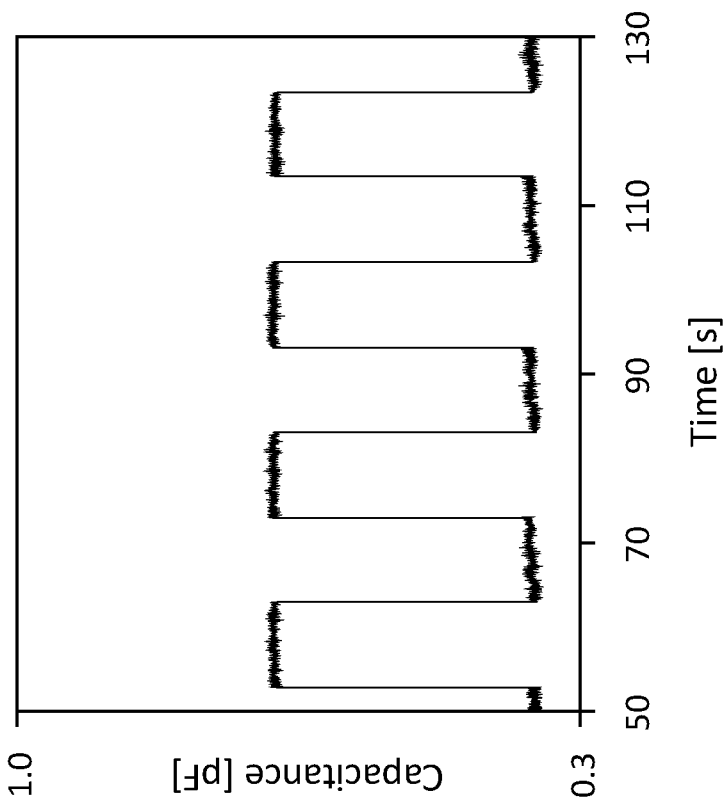
Figure 11D:
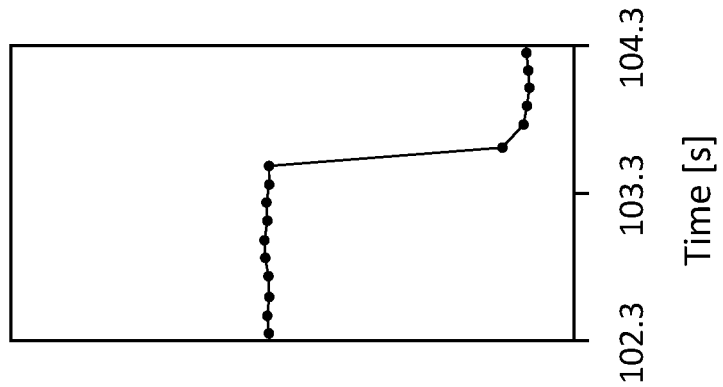
Figure 11C:
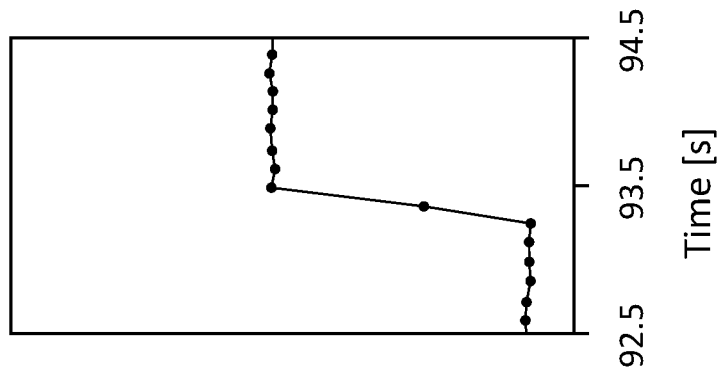

The pressure sensitivity S is defined as the slope of the traces, $S=\delta(\Delta C/C_{min})/\delta P$, where C and $C_{min}$ are the impedances with and without applied pressure, and P is the applied pressure. The normal pressure sensitivity for the capacitors located at the top of the domes, is $0.19\pm0.07$ kPa$^{-1}$ in the low-pressure regime (P<1 kPa), $0.10\pm0.01$ kPa$^{-1}$ in the range 1<P<10 kPa, and $0.04\pm0.001$ kPa$^{-1}$ in the range 10<P<20 kPa. The pressure sensitivity is on average 68% and 30% of these values for the capacitors located on the slope and at the bottom of the domes, respectively. Moreover, the measured response time may be within the millisecond range (as further illustrated FIGS. 11A-11B).

In specific experimental embodiments, the sensitivity to shear force, for the capacitors located at the top and side of the dome-shaped microstructure exposed to shear force, is $3.0\pm0.5$ Pa$^{-1}$ (10<P<20 kPa). The sensitivity of the capacitors located on the side of the dome-shaped microstructure not exposed to shear force is on average 30% that of the exposed side. Each capacitor associated a respective dome-shaped microstructure, depending on its location on the dome-shaped microstructure, reacts differently to the same applied force. For example, the dome-shaped microstructure concentrate forces onto the receptors differently depending on the direction of applied force as shown by FIG. 5D. At pressures below 70 kPa, the capacitors at the top of the dome-shaped microstructure can have a higher sensitivity than the capacitors at the bottom of the dome-shaped microstructure, due to the short capacitor gap and the deformation of the pyramid-shaped microstructures upon applied pressure. On the other hand, the capacitors located at the side of the dome-shaped microstructure can have a better ability to measure larger forces without reaching saturation: above 70 kPa, the capacitors surrounding the dome-shaped microstructures can have a pressure sensitivity 9% higher (range 100 to 600 kPa) than the capacitors at the top of the dome-shaped microstructures, because of the deformation of the top membrane.

Figure 5G:
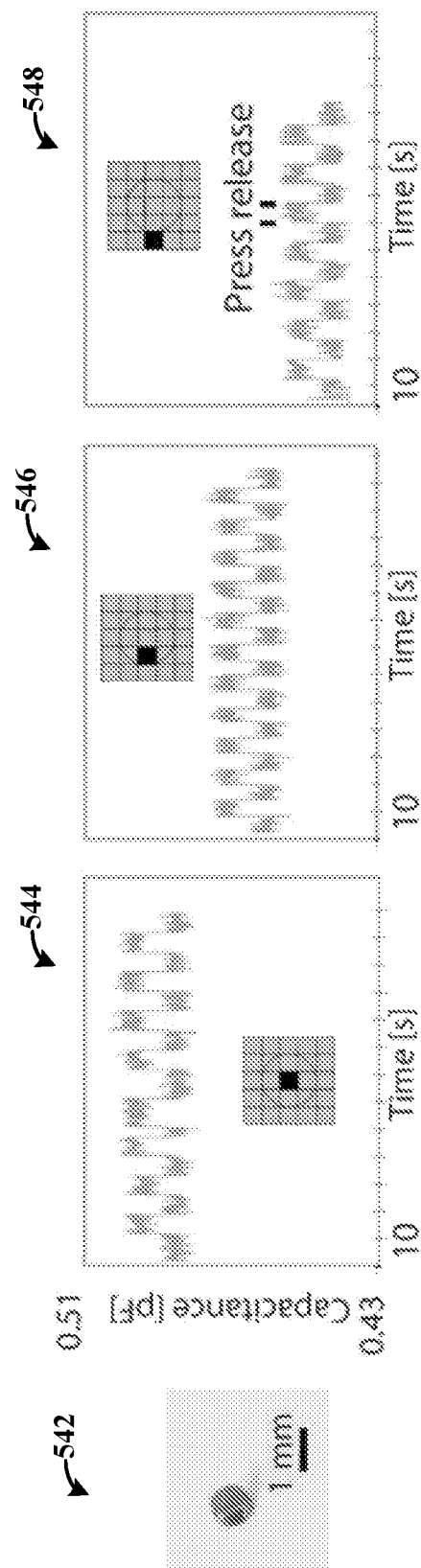
Figure 5H:
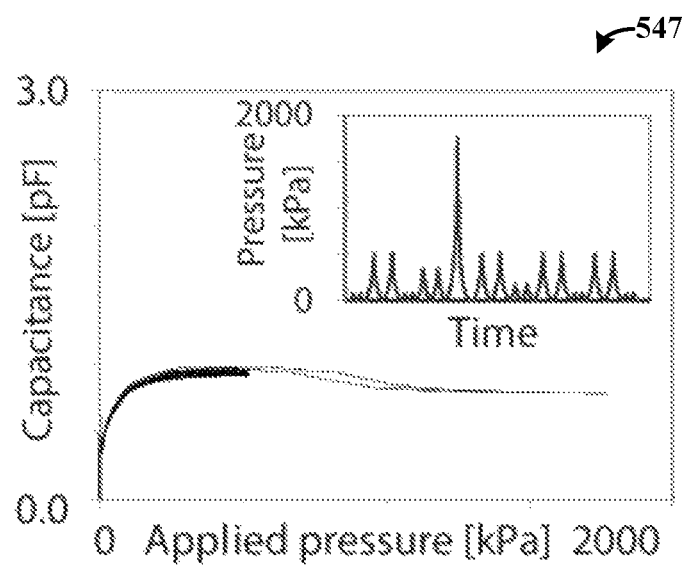
Figure 5I:
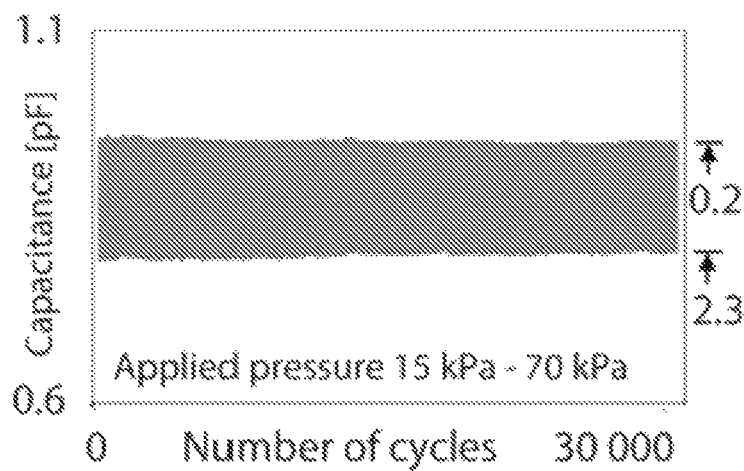

As shown by FIGS. 5E-5I, because of the stretchability of elastomer, the sensor apparatus enables the detection of a force exerted on a localized area with limited effect on nearby pixels, as demonstrated with a 9×9 sensor array. In a specific example, the sensor apparatus is designed to work in a range up to a maximum of 100 kPa, a little higher than the typical human touch sensitive range (~10 kPa). Such a sensor in robotic application also can be robust to high-pressure events, such as shown by FIG. 5H. For several consecutive runs of pressures 0 to 1800 kPa, the sensor output is reproducible and the characteristic of the device may not be altered by the high pressures. Further, the sensor apparatus is sensitive and can detect small weights of 15 mg, as shown by FIG. 5G, corresponding to pressure <0.5 kPa. In such experimental embodiments, a real-time signal-to-noise ratio (SNR) of 3 is calculated. In a number of embodiments, the baseline signal is higher and a greater SNR is obtained. Moreover, the pressure response of the sensors can be reproducibly cycled thousands of times, as shown by FIG. 5I. After applying a pressure of 70 kPa and releasing to 15 kPa for more than 30,000 cycles (duration of 1 cycle: 4 seconds), $C_{min}$ and $C_{max}$ increase by 2.3% and 0.2%, respectively.

FIGS. 5E and 5F illustrate three dimensional plots 541, 543 of the measured relative change in impedance in a sensor array 537, 539 of 9×9 capacitors, where each shaded band corresponds to a variation $\Delta C/C_{min}=5\%$. Normal force applied on the entire 9×9 array, as shown by the sensor array 537 and on the bottom left corner, as shown by the sensor array 539. The pixels (e.g., capacitors) located proximal to the top of the dome-shaped microstructures have a measured standard deviation on $\Delta C/C_{min}$ below 20%.

FIG. 5G illustrates example repeated measurements related to an object. The sensor apparatus may be sensitive enough to measure objects as small as the illustrated 1 mm-diameter plastic bead 542 (15 mg, corresponding to less than 0.5 kPa). The bead 542 is placed on the sensor array (zone 2) and removed several times, and the pressure response signal is measured for capacitors located at the top (as illustrated by the first graph 544), at the slope (as illustrated by the second graph 546) and at the bottom (as illustrated by the third graph 548) of the dome-shaped microstructure.

FIG. 5H illustrates a graph 547 of sensor apparatus responses at applied pressures in the range 0 to 1800 kPa (normal force, pyramids width a=30 µm, separation distance between the pyramids b/a=2 where a+b is the distance between the centers of 2 pyramids). The robustness of the sensor is illustrated by the unaltered pressure response curves after several runs at various pressures (shown in inset). FIG. 5I illustrates a graph 549 showing results of a cycling test which illustrate the stability of the pressure response over 30,000 cycles (a=30 µm, b/a=2). A small signal drift is measured, illustrated by the fact that $C_{15\ kPa}$ (capacitance measured when 15 kPa is applied) increases by 2.3% and $C_{80\ kPa}$ (capacitance measured when 80 kPa is applied) increases by 0.2% after 30,000 cycles. In all figures, the pyramids are arranged in a 2D orthogonal grid, the width of the pyramids is a=30 µm and the separation distance between the pyramids is b/a=4 unless stated otherwise.

The differing behaviors allow for sensor circuitry to differentiate between normal, shear, and tilt forces. The sensor circuitry may be used to identify the type of force, the direction of the force, and the magnitude of the force based on the resulting patterns illustrated by a respective array of capacitors and/or of a plurality of arrays.

The sensor circuitry can measure dynamic force by using the same transduction technology used for the static force by applying a high sampling rate (>500 Hz). In specific embodiments, the sensor circuitry includes at least one CDC circuitry that connects at least some of the electrodes to an input channel of the CDC circuitry. The sensor circuitry can measure dynamic forces by measuring impedance at a sample rate using the CDC circuitry and connected processing circuitry (e.g., microcontroller). To measure dynamic force by such a sampling rate, the sensor uses two CDC circuitry (e.g., CDC chips) to connect the four electrode pairs to 2 of the 12 analog input channels of each chip, since a high sampling rate (>500 Hz) can be obtained from a lower number of capacitor inputs to the chip. The CDC chip consists of a sigma-delta-based CDC with 12 analog input channels and communicates with a microcontroller via an I2C bus, measuring capacitance in 0.3-1.2 kHz sampling rate, and cancelling noise from capacitors through active shield function. For more information on CDC chips and active shield function, reference may be made to AD7147, Analog, http://www.analog.cm/media/en/technical-documentation/data-sheets/AD7147.pdf.

In various embodiments, the sensor apparatus is configured to be in contact with a finger. For example, FIGS. 4A-4B of the underlying provisional application show an example experimental sensing apparatus, consistent with embodiments of the present disclosure. More specifically, FIG. 4A of the underlying provisional application illustrates sensor circuitry in contact with a human finger. The sensor circuitry is thin and flexible such that it can cover the curved finger surface. FIG. 4B of the underlying provisional application illustrates sensor circuitry in communication (wired or wireless) with processing circuitry. The sensor circuitry can be connected to the processing circuitry, such as a laptop computer, by a printed circuit board. The processing circuitry can receive the signal data from the sensor circuitry and provide a graphical display of the resulting applied force on the sensor circuitry (e.g., the graph).

Figure 6A:
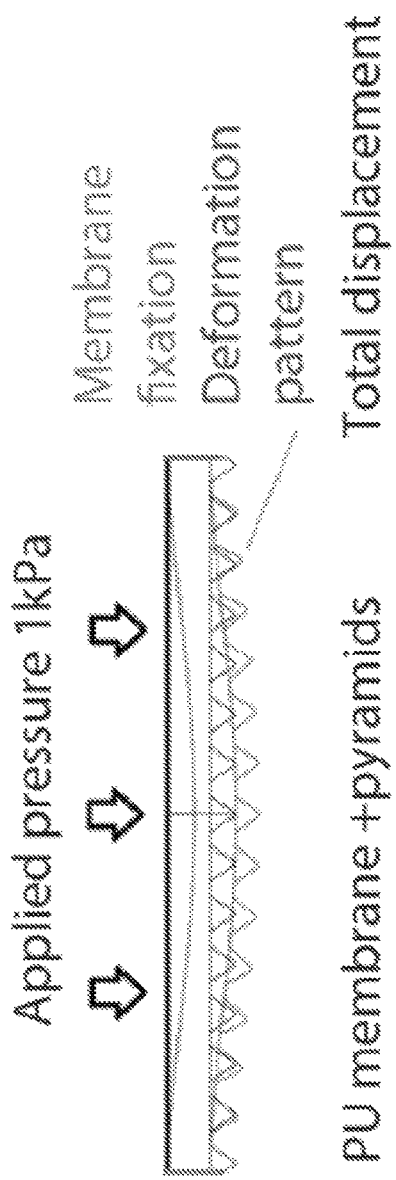

FIGS. 6A-6H show an example of a sensor apparatus under different forces, consistent with embodiments of the present disclosure. More specifically, FIGS. 6A-6D illustrates an example of sensor apparatus designed with the objective to maximize the sensitivity, the signal-to-noise ratio (SNR) and the time-response. The geometry of the pyramid-shaped microstructures may be optimized based on geometry of the pyramids (e.g., size, ratio b/a) for the deflection of the top membrane in zone 1, corresponding to the capacitors located on the slopes and at the bottom of the dome-shaped electrodes. For this purpose, various pyramid sizes (e.g., width 10, 20, 30, 40 and 50 µm) and separation distances (e.g., ratio b/a=0.4, 0.8, 1.2, 1.6, 2 and 4, where a+b is the distance between the centers of two pyramids) are investigated. Zone 1 capacitors are located on the slopes and bottom of the domes/hills and zone 2 capacitors are at the top of the domes/hills. FIG. 6H illustrates the different changes in structure, as well illustrating as zone 1 and zone 2.

Figure 6B:
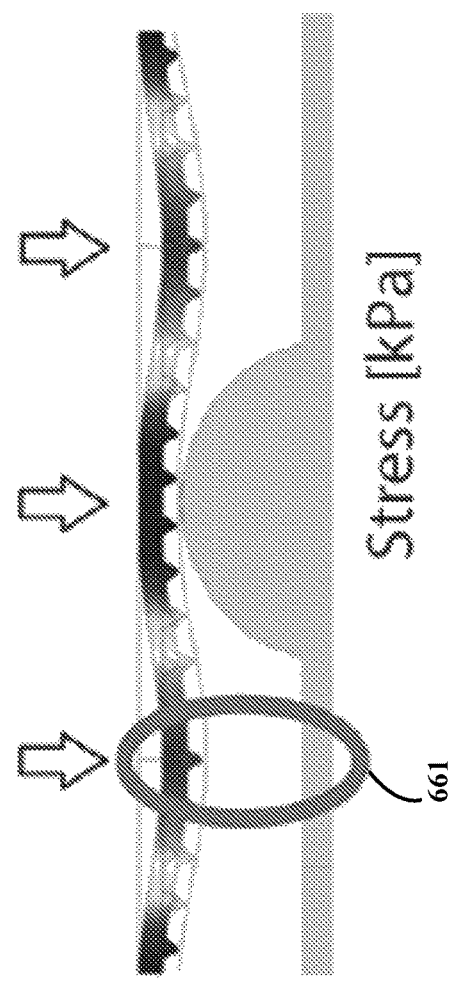
Figures 6C, 6D, 6E:
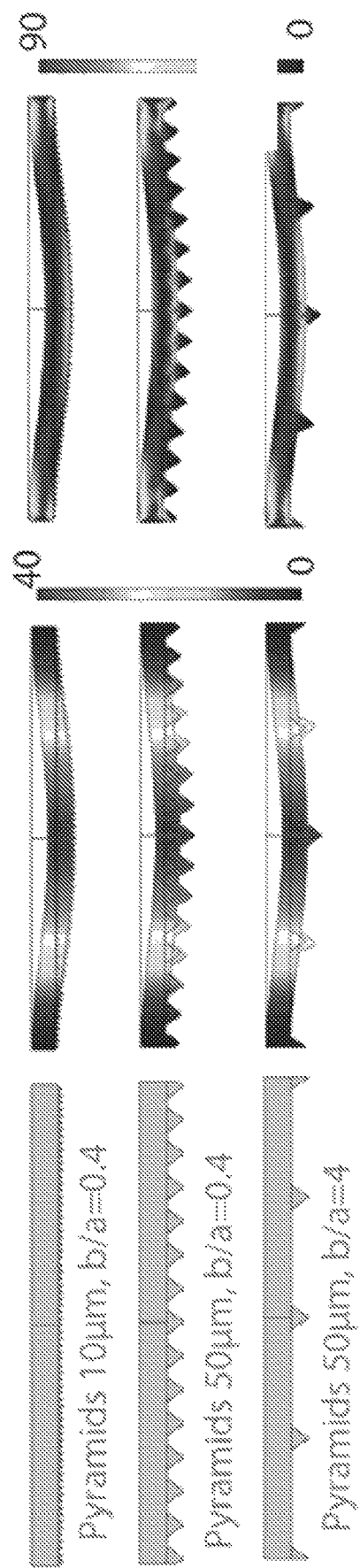

FIG. 6A illustrates a cross sectional view of the first substrate having pyramid-shaped electrodes in zone 1. A 1 kPa uniform pressure is applied (normal force). The initial and deformation patterns are shown, respectively. FIG. 6B illustrates the cross sectional view of the deformation pattern of the first substrate with the pyramid-shaped electrodes in response to applying the 1 kPa uniform pressure. Additionally shown is zone 1 661. FIGS. 6C-6E illustrate simulations performed for pyramid widths of 10, 20, 30, 40 and 50 μm, and separation distances between the pyramids of b/a=0.4, 0.8, 1.2, 1.6, 2 and 4 (a+b is the distance between the centers of two pyramids).

COMSOL simulations for zone 1 and zone 2 are performed with the objective to maximize the deflection of the top membrane upon applied pressure. Following the parallel plate capacitor definition of C, this results in larger $\Delta C/C_{min}$:

$$C = \varepsilon_r \varepsilon_0 A/d \quad (1)$$

where $\varepsilon_r$ is the relative static permittivity, co is the permittivity of vacuum, A is the area of overlap of the two electrodes and d is the separation between the electrodes.

FIGS. 6F-6G show results for total displacement (e.g., FIG. 6F) and stress (e.g., FIG. 6F). The distance evaluated for total displacement is indicated with arrows. The stress is evaluated at the point indicated with the circle 613. Then the circle 611 identifies optimized conditions for high sensitivity. The influence on $\Delta C/C_{min}$, when comparing worst case scenario (a=50 μm, b/a=0.4) and the optimized scenario (a=10 μm, b/a=4, applied pressure 1 kPa) is ~4%. FIGS. 6F-6G show that higher top membrane deformation is achieved in zone 1 615 with smaller pyramids and larger separation distance, resulting in larger $\Delta C/C_{min}$ and larger sensitivity. Moreover, according to equation (1), in zone 2 616, larger $C_{min}$ and therefore better SNR are achieved with smaller pyramids and smaller separation distance between the pyramids, as further illustrated by FIGS. 12A-12D. In addition, it is shown that faster response time is achieved with smaller separation distance between the pyramids.

FIG. 6H shows a summary for an optimized sensor apparatus, in terms of pyramids microstructure design. To optimize the sensor apparatus, the positions of pyramids are adjusted in order to fulfill the requirements for both zone 1 and 2 615, 616. A spiral grid or pattern gives a good combination of high sensitivity in zone 1 615, and high $C_{min}$ and fast time response in zone 2 616. This distribution offers a smooth transition of pyramids density from zone 1 to 2, from large to small ratio b/a, respectively. Spiral grids may include so-called phyllotaxis spirals. An example phyllotaxis spiral is shown by a capitulum of sunflower (e.g., FIG. 5d of the underlying Provisional Application), where multiple spirals run both clockwise and anticlockwise. Mathematically, phyllotaxis spirals can be calculated using the planar model proposed by Helmut Vogel. This model is based on an analysis of the Fibonacci suite converging at infinity towards the golden number, where every number is the sum of the two preceding ones. The position of each pyramid from the center is defined with the formula:

$$\varphi = n * 137.5°, \quad r = c \, n^{1/2} \quad (2),$$

where n is the numbering order of each single pyramid. The scaling parameter controls the phyllotaxis pattern. Based on this formula, sensor apparatuses are fabricated, where the pyramids are not positioned according to orthogonal grids, but according to phyllotaxis spiral grids with one spiral per dome (e.g., FIGS. 7A-7G). The top electrode with pyramids are seen to be organized along a phyllotaxis spiral grid (e.g., FIG. 7H), ready for sensor assembly.

Figure 7G:
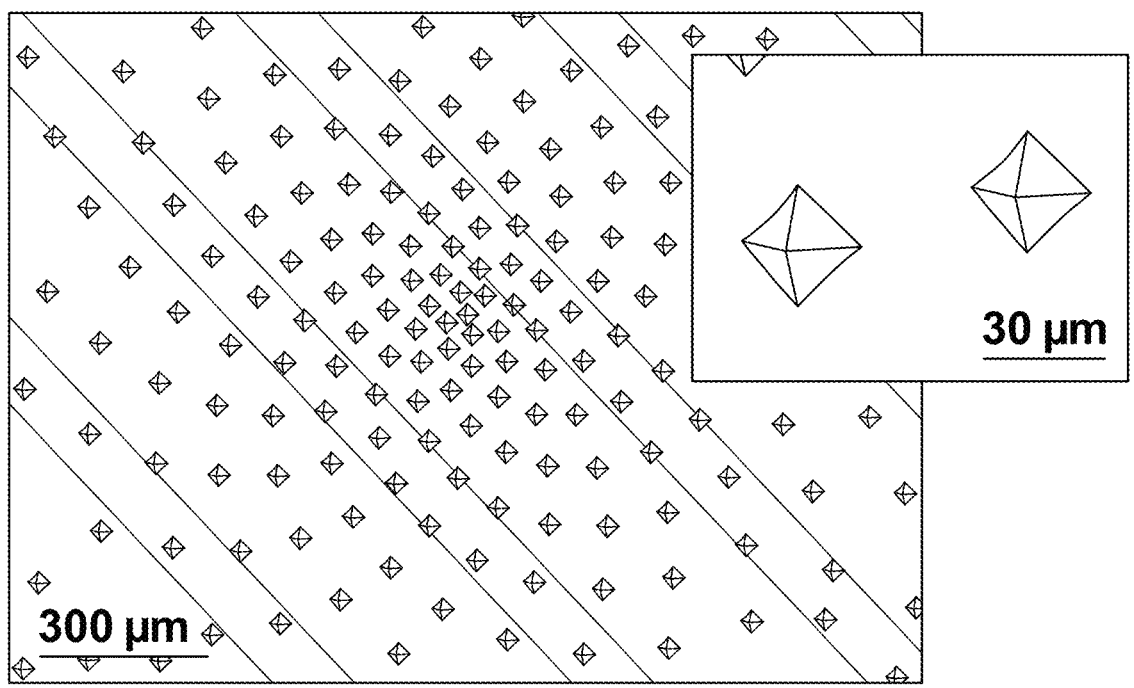

FIGS. 7A-7G show example microstructure patterns, consistent with embodiments of the present disclosure. FIGS. 7A and 7B illustrate microscope images of the Silicon (Si) masks used to mold the PU top electrode, with pyramids arranged along orthogonal grid. FIGS. 7D and 7E illustrate microscope images of the Si masks used to mold the PU top electrode, with pyramids arranged along spiral grids. FIGS. 7C and 7F illustrate the domes shown at the same scale as the top electrode with pyramids. As previously described the top electrode layers are positioned on the 1 mm-diameter domes shown at the same scale. FIG. 7G illustrates an SEM image showing the PU top electrode layer with pyramids arranged along phyllotaxis spiral grid. The CNTs-PU conducting electrodes appear as stripes of light grey (stripes of darker grey correspond to PU without CNTs between the electrodes).

Figures 8A, 8B, 8C, 8D:
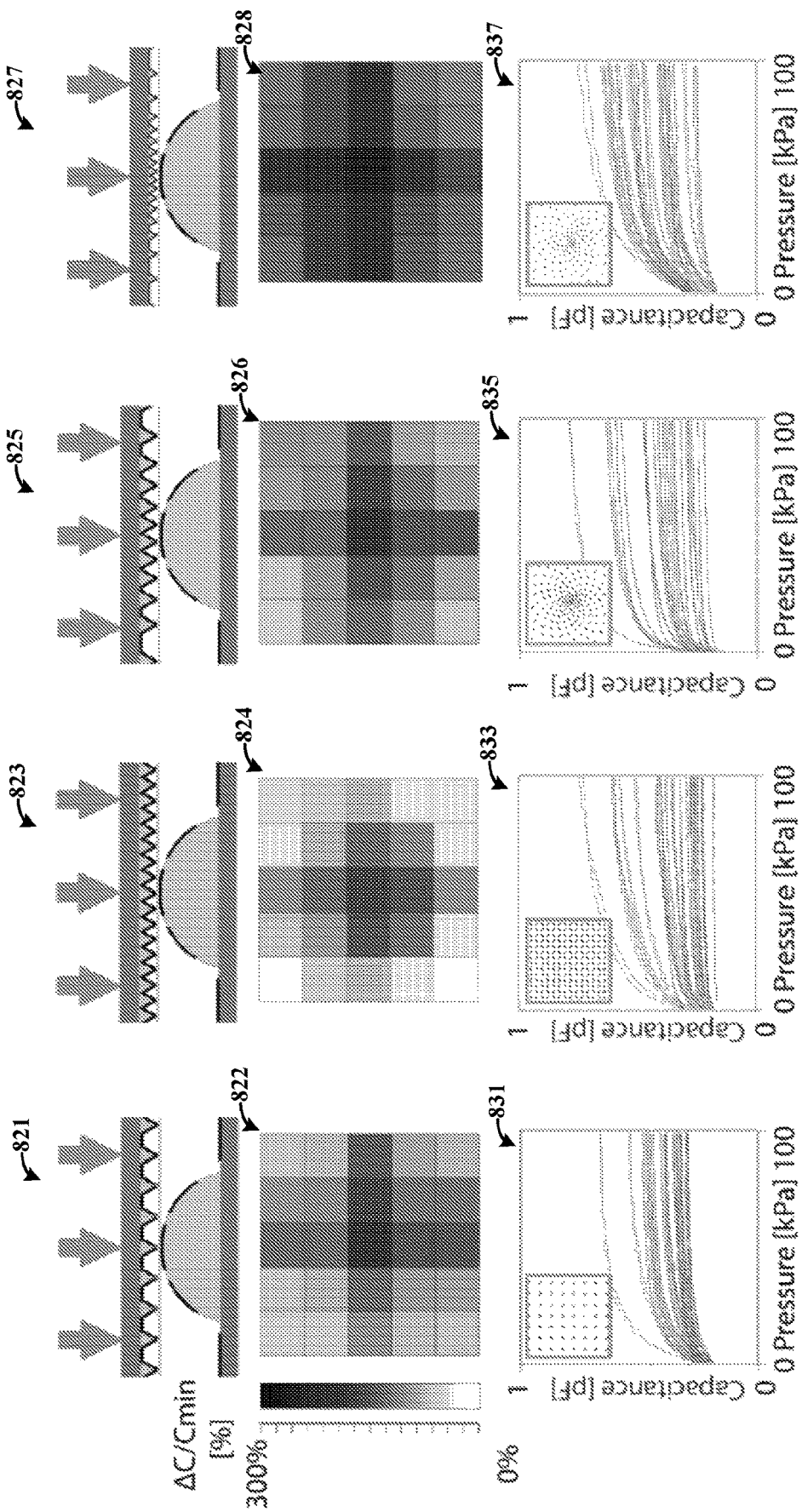
FIGS. 8A-8D show an example sensor apparatus under different forces and resulting capacitive patterns, consistent with embodiments of the present disclosure.

FIGS. 8A-8D show an example sensor apparatus under different forces and resulting capacitive response patterns, consistent with embodiments of the present disclosure. The response characteristics of the sensor apparatus, for sensor arrays of 5×5 capacitors with orthogonal and spiral pyramids grids are shown in FIGS. 8A-8D. More specifically, FIG. 8A illustrates 30 μm-wide pyramids positioned along an orthogonal grid with ratio b/a=4. FIG. 8B illustrates 30 μm-wide pyramids positioned along an orthogonal grid with ratio b/a=0.4. FIG. 8C illustrates 30 μm-wide pyramids positioned along a phyllotaxis spiral grid (ratio b/a=0.4 and 4 at the spiral center and border, respectively). FIG. 8D illustrates 10 μm-wide pyramids positioned along a phyllotaxis spiral grid (ratio b/a=0.4 and 4 at the spiral center and border, respectively). Each of FIGS. 8A-8D illustrate a cross-sectional side view 821, 823, 825, 827 of the sensor array with κ×5 capacitors, and with a normal force illustrated by the arrow. Further, FIGS. 8A-8D illustrates capacitive maps 822, 824, 826, 828 showing the relative change in capacitance $\Delta C/C_{min}$ for the twenty-five capacitors of each array. And, the graphs 831, 833, 835, 837 illustrates the response curves for the twenty-five capacitors of each array.

Considering zone 1, larger $\Delta C/C_{min}$ are measured with devices in FIGS. 8A and 8C, where the separation distance between the pyramids is large (ratio b/a=4 vs. 0.4 in FIG. 8B). This result is in agreement with simulations (e.g., FIGS. 6A-6G). Moreover, FIGS. 8C and 8D show the response curves for two sensor arrays with spiral grids, with pyramids width 30 μm and 10 μm, respectively. The difference in concentration or intensity between the center and edge is less distinct with spiral grids (e.g., FIGS. 8C and 8D) than orthogonal grids (e.g., FIGS. 8A and 8B), corresponding to larger response curves and $\Delta C/C_{min}$ measured at the border of the hills in the context of spiral grids. In addition, larger $C_{min}$ and better SNR are achieved with smaller pyramids (e.g., FIG. 8D). These results illustrate the superiority of the spiral grids compared to orthogonal grids.

FIGS. 9A-9F show example performance of a sensor apparatus, consistent with embodiments of the present disclosure. Robotic experiments may be performed, as shown, with the objectives to demonstrate the use of the e-skin to control a robot arm in real time, and that the high sensitivity of the nature-inspired e-skin for normal force and shear force stimuli enables tasks requiring high dexterity.

Figure 9A:
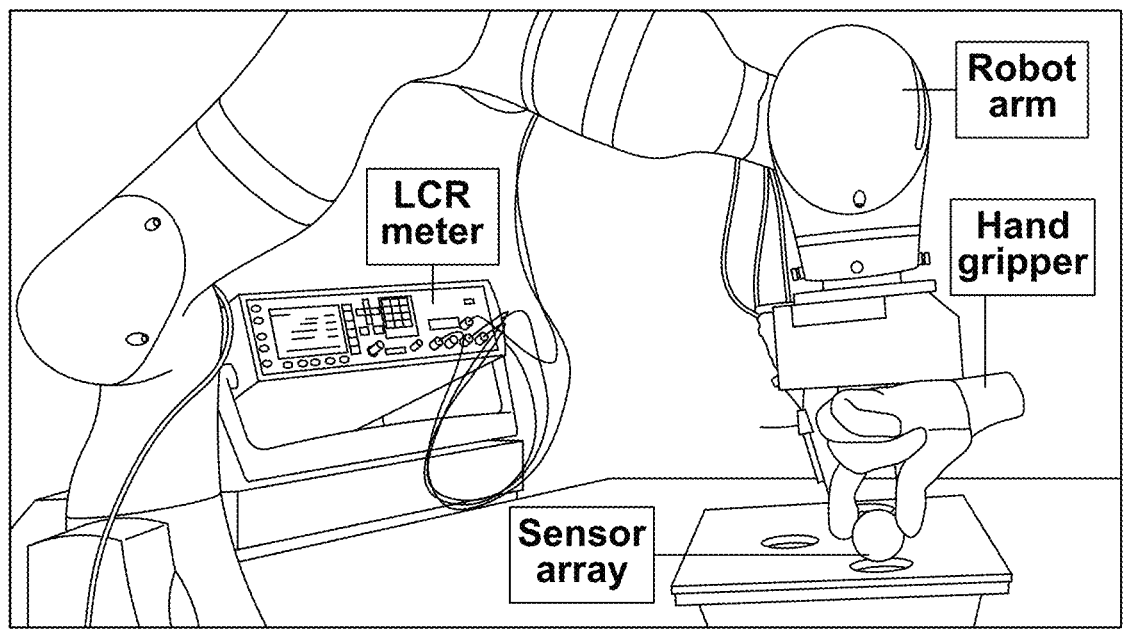
FIGS. 9A-9F show example performance of a sensor apparatus, consistent with embodiments of the present disclosure.

FIG. 9A shows example experimental set-up which includes a sensor array mounted on an artificial hand and fixed on a gripper that is attached to a robot arm. The limitations of a single pixel detection experimental set-up prevents integration of the full directional sensing capabilities in robotic application, which requires developments of a multiplexing acquisition platform. An LCR (inductance (L), capacitance (C), resistance (R)) meter is recording the capacitance signal from sensor array. Data is stored on a server and retrieved by the robot controller to be used in a closed-loop feedback scheme to control the movement of the robot arm in real time.

Figure 9B:
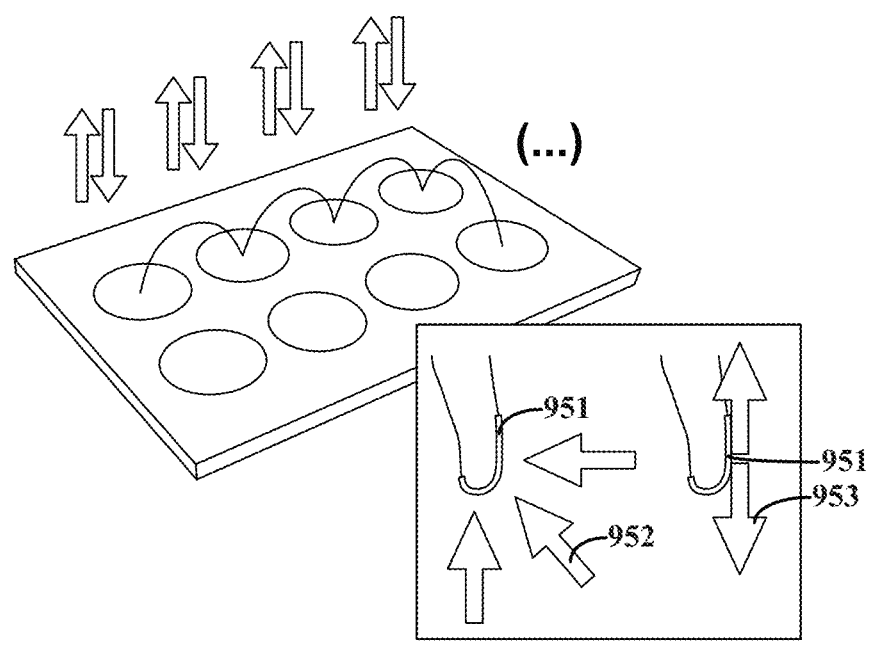

This design has the advantage of making the mechanical structure of the sensor independent from the movement of the arm, thus the only measurement obtained is the contribution of the pressure and shear forces. FIG. 9B (as well as FIG. S7 of the underlying provisional application) show an example test-plate with holes, and the pre-programmed consecutive movements executed by the robot arm, unless tactile feedback prevents the execution of the entire movement downwards. The sensor array 951 is either exposed to normal force (e.g., arrows 952) or shear force (e.g., arrows 953). Illustrated is an example test-plate with holes (e.g., either 8 holes, 4 holes, or no hole, as illustrated in FIGS. 9D and 9F). The lines show the consecutive movements executed by the robot arm, unless tactile feedback prevents the entire execution of the down movement.

Figure 9C:
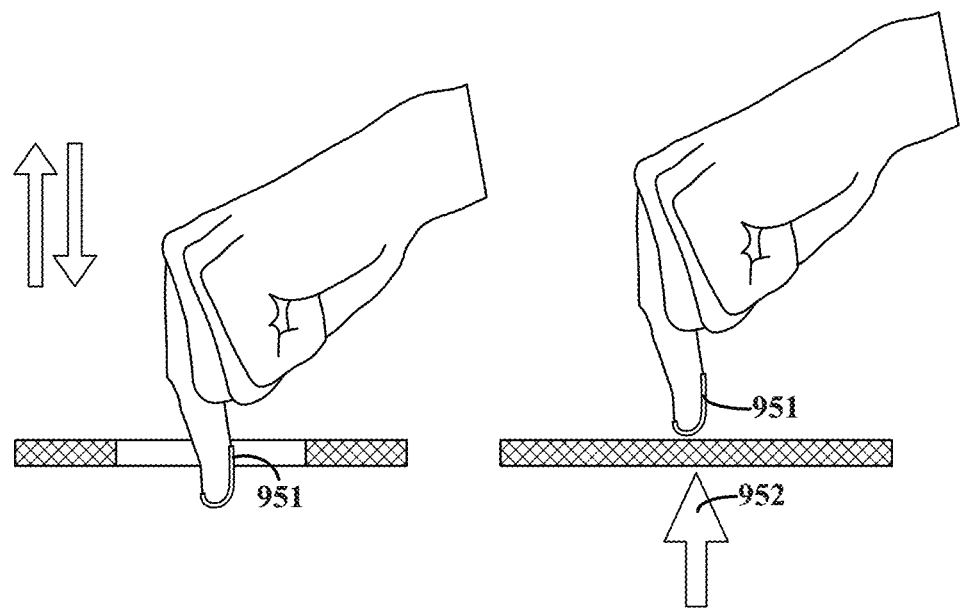
Figure 9E:
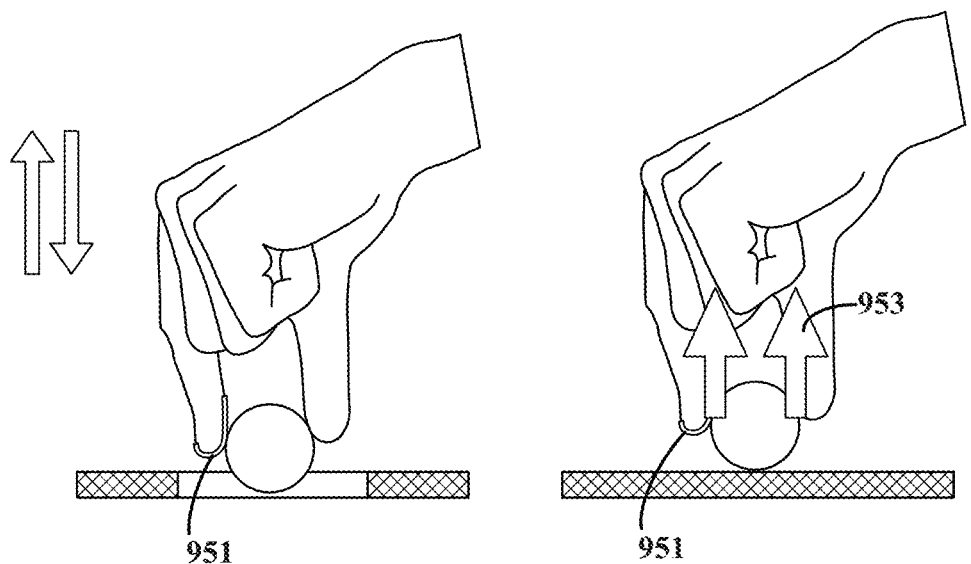
Figure 9D:
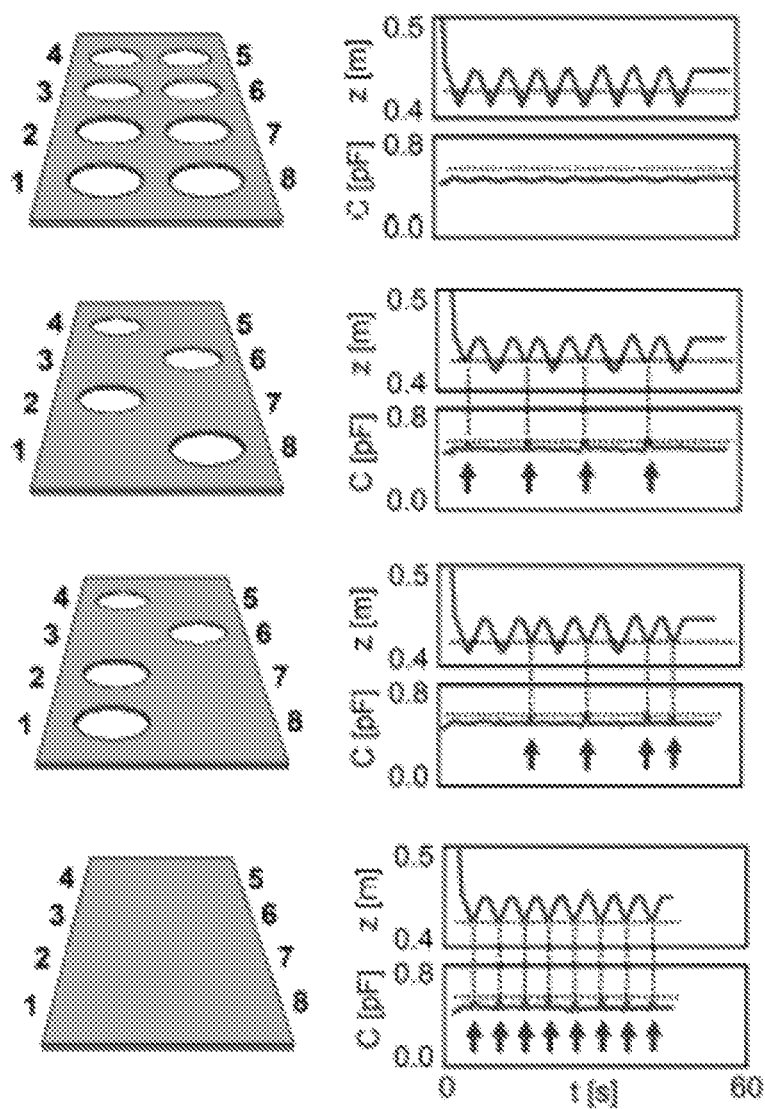
Figure 9F:
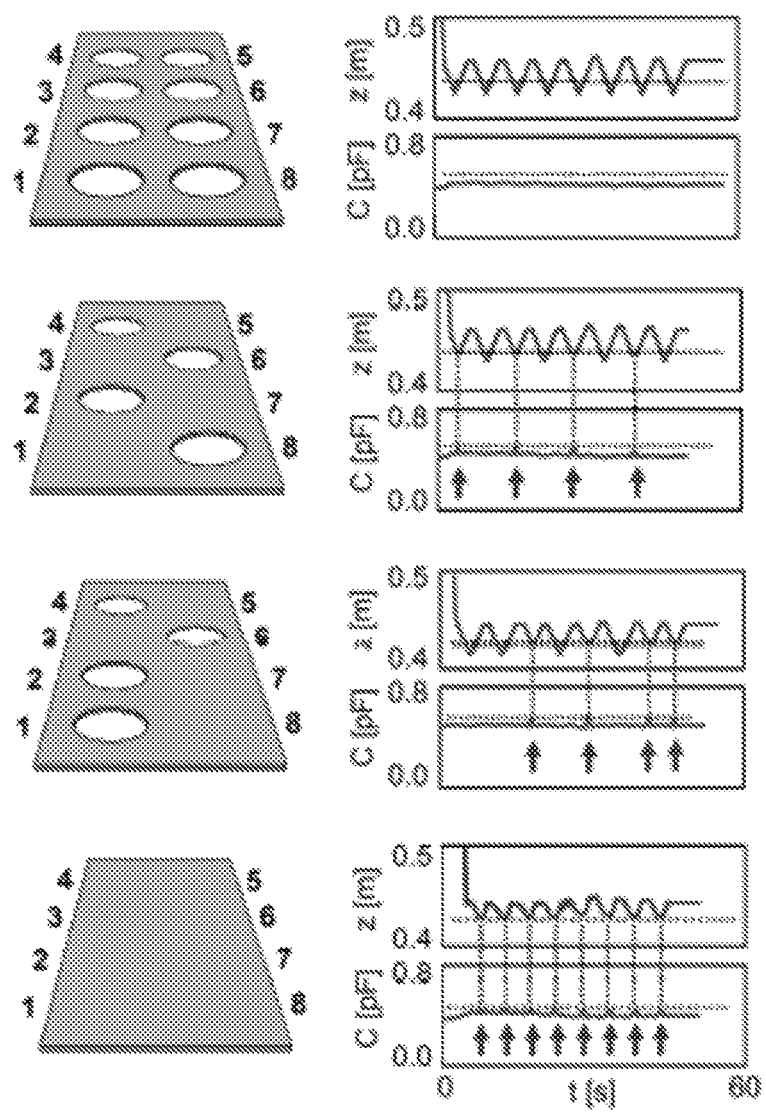

When the sensor array is solely exposed to normal force, the robot arm correctly executes a premature movement in upwards direction as soon as the finger touches the test plate at a location with no hole due to sensing of a normal force (arrow 952), as shown by FIGS. 9C-9D. More specifically, FIG. 9C illustrates a set of experiments where the sensor array is solely exposed to normal force is reproduced three times. The arrows show the movement executed downwards, unless normal force feedback 952 is detected and prevents the entire execution of the movement downwards. FIG. 9D illustrates example experiments performed with 4 different test-plate with holes. The robot arm goes consecutively from position 1 to position 8. For each experiment, the position of the robot arm in z-direction and the measured capacitance C are plotted as a function of time. The arrows in the graph indicate the successful detection of normal force when the finger touches the plate (in the absence of a hole), and the corresponding close-loop control feedback movement in upwards direction.

FIG. 9E illustrates a second set of experiments in which the sensor array is solely exposed to shear force, reproduced three times. If the sensor array is solely exposed to shear (tangential) force with a light object (ping pong ball, weight 2.7 g) placed between the two artificial fingers, shear force (e.g., arrow 953) is exerted on the sensor array as soon as the robot arm goes vertically down and the ball is pressed on the table. The arrows show the movement executed downwards, unless shear (tangential) force feedback 953 is detected and prevents the entire execution of the movement downwards. Because of the light weight, only a negligible tangential force contribution due to the weight (gravity) is initially present. FIG. 9F show example experiments performed with four different test-plates with various numbers of holes. The arrows in the measured capacitance plots indicate the successful detection of shear force. When the ping pong ball touches the table below, it is observed that it is not sliding between the fingers because of the initial small normal force applied to hold it and because of the surface interaction between polyurethane and the ball. It is therefore the tangential force that is measured by the sensor array that is used to control the robot movement. As soon as tangential force is measured the robot stops its movement downwards, goes back up and continue the experiment to the next position.

It is shown in FIG. 9F that the robot arm correctly interrupts its pre-programmed movement in downward direction as soon as shear force is detected and the ball touches the test plate at a location with no hole. FIGS. 6g to 6i of the underlying Provisional Application also illustrate the high sensitivity of the sensor and demonstrate the tactile sensing capabilities allowing to interact with deformable and delicate objects such as a fresh raspberry. The tactile feedback may be used to prevent the raspberry from being flattened.

Embodiments in accordance with the present disclosure include a biomimetic flexible e-skin composed of an array of capacitors, capable of measuring and discriminating in real time both normal and shear forces. The e-skin is used to control a robot arm in various tasks as a first step towards integration of its high-sensitivity directional sensing capabilities, illustrating its potential future application in various fields of robotics including personalized domestic help, ambulatory and inpatient health care, medical diagnosis, surgery, industry, and exploratory missions in hard to reach places.

In various experiments shown in FIGS. 5A-9F data collection rules are based on pressure ranges predefined prior to each experiment. A pressure gauge or the robotic hand controller automatically reverses upon detection of a pressure maxima. Outliers are identified by analyzing SNR of the response curve, which allows for identification of faulty sensor fabrication or bad connectivity at the interfaces. In those cases, either the sensor is eliminated from the test batch, the two electrode layers are realigned, or connectivity with LCR is adjusted. Experiments are then reproduced with the new sensor.

Fabrication of the silicon (Si) wafer with pyramid grids may include Si wafers patterned with pyramids of different sizes by lithography followed by HF oxide etching and finally an anisotropic potassium hydroxide (KOH) etching.

Patterning of the CNT electrodes on polyurethane substrate may include a fabrication step applied to both the top and bottom PU electrodes. Si wafers are cleaned with O2-plasma. A CNTs-layer is spray-coated on the wafers from a CNTs dispersion (12 mg of P2-SWNT from Carbon Solutions and 70 mL of N-methyl-2-pyrrolidone ultrasonicated for 30 minutes followed by collecting the supernatant after centrifugation for 30 minutes at 8000 rpm, 18 degrees C.). The CNT electrodes are lithographically patterned using S1813 photoresist. For the top electrode with pyramid grid, the photolithography mask is aligned with the pyramids, to ensure a proper positioning of the CNT electrodes. A subsequent oxygen plasma etching is used to remove the CNTs without photoresist protection. The remaining photoresist is then removed using acetone, isopropanol and water. On this wafer, polyurethane elastomer (Tecoflex SG-80A from Lubrizol Co.) is cast from chloroform solution (10 mg/mL) by spin-coating at 1000 rpm, followed by another layer of polyurethane from chloroform solution (60 mg/mL) at 1000 rpm. The first layer is used to promote adhesion to CNTs, while the thicker layer (~10 μm) allows for manipulation of the electrodes. The PU films with CNTs-patterned electrodes are then released from glass substrate for sensor assembly.

Fabrication of the domes/hills arrays may involve CNTs-patterned PU electrode film (without pyramids) being placed on a grid with 1 mm holes, with the CNTs lines aligned with the grid (three lines per hole, one line in between each hole, as shown in FIGS. 1b and 3b (inset) of the underlying Provisional Application). Vacuum (~250 Torr) is applied to create the hill shape in PU. A Polydimethylsiloxane layer (ratio 1:10, thickness~3 mm, PDMS Sylgard from Dow Corning Co.) is cast onto the electrode film, then oven-baked for 30 min at 80 degrees C. The final bottom electrode with domes/hills is then released and ready for assembly.

The sensor is assembled by laminating the bottom electrode with hills, the 10 μm-thick polyhydroxybutyrate-polyhydroxyvalerate (PHB-PHV) dielectric layer, and the top electrode with pyramids. During lamination, the two electrodes are aligned perpendicular to each other so that each dome/hill corresponds to twenty-five capacitors (one on the top of the dome/hill, four on the slopes, four on the "corners", and sixteen shared capacitors surrounding the dome/hill). The alignment is made manually using an optical microscope. Moreover, PHB-PHV is selected as dielectric because it combines good mechanical resistance at low thickness and moderate dielectric constant to maximize for capacitance, as described in Equation 1.

As shown by FIG. 9A-9F, force response measurement setup may involve and/or consists of a motorized vertical stage used in combination with a force gauge, while the capacitance of each sensor was measured with an LCR meter.

The e-skin is fixed on a mock-up flexible hand, which is attached to a Schunk WSG 50 gripper mounted on a robot arm (KUKA IIWA). The robot is programmed to perform series of predefined movements, as defined by the experimental protocol, with a controller that can stop the movement depending on the signal recorded on the e-skin. The control algorithm takes as input the signal from the e-skin through the LCR and stops the movement of the robotic arm if the signal reaches a predefined capacitance threshold. A redis interface is used for the communication between the LCR and the computer controlling the robot.

Figure 10C:
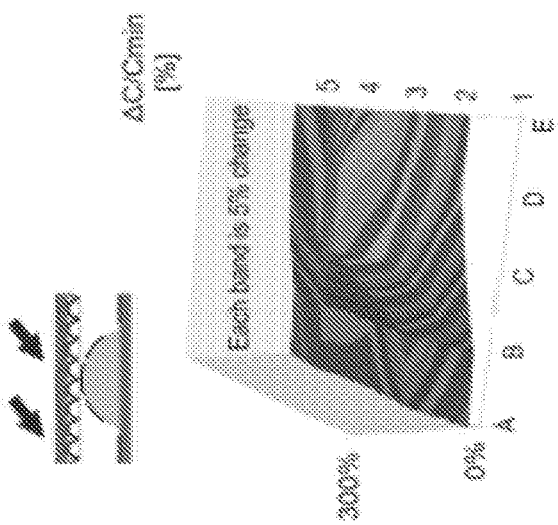
FIGS. 10A-10C show an example of a sensor apparatus under different forces, consistent with embodiments of the present disclosure.
Figure 10B:
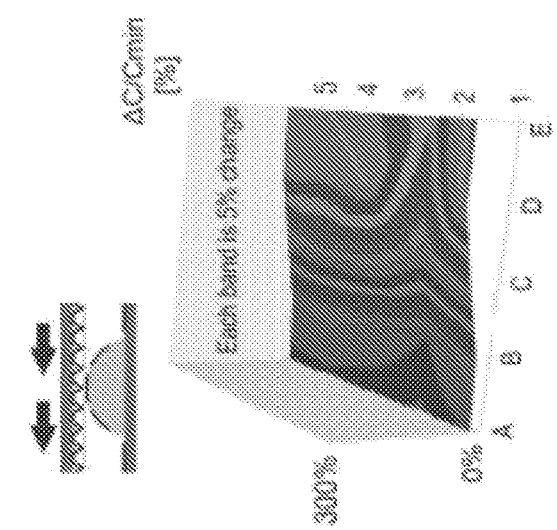
Figure 10A:
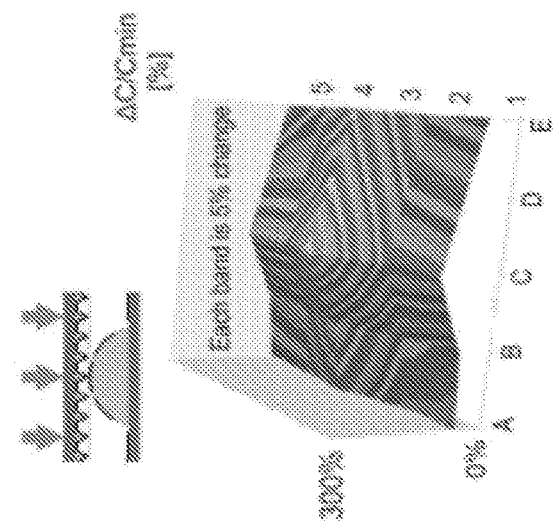

FIGS. 10A-10C show an example of a sensor apparatus under different forces, consistent with embodiments of the present disclosure. A sensor array of 5×5 capacitors, centered on one dome, is characterized by measuring the pressure response curve upon an applied normal force (as shown by FIG. 10A), an applied shear force (as shown by FIG. 10B), and an applied tilt force (as shown by FIG. 10C). FIGS. 10A-10C show respective 3D plots where each color band corresponds to a variation $\Delta C/C_{min} = (C_{700\ kPa} - C_{min})/C_{min} = 5\%$, where $C_{min}$ and $C_{700\ kPa}$ are the capacitances without and with applied pressure, respectively.

FIGS. 11A-11D show example performance of a sensor apparatus, consistent with embodiments of the present disclosure, such as using the experimental set up illustrated by FIG. S3 of the underlying provisional. More specifically, FIGS. 11A-11D show an immediate response of the sensor array when a constant pressure is applied and then released (here 20 kPa for about 10 s). The underlying provisional application illustrates an example experimental set up for applying normal, shear, and tilt forces to a sensor array.

Figure 12A:
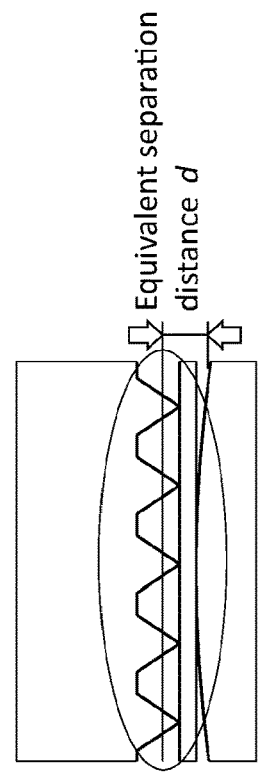
FIGS. 12A-12D show example microstructure patterns, consistent with embodiments of the present disclosure.
Figure 12B:
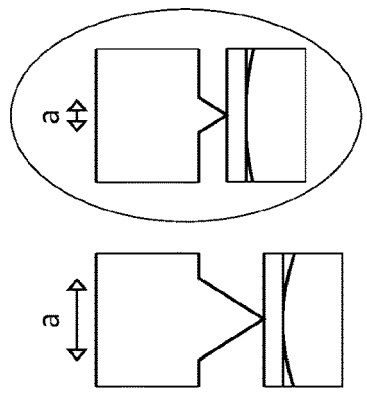
Figure 12C:
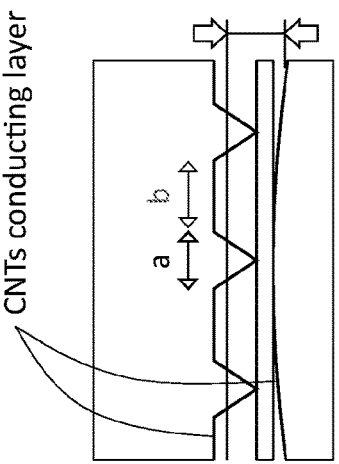
Figure 12D:
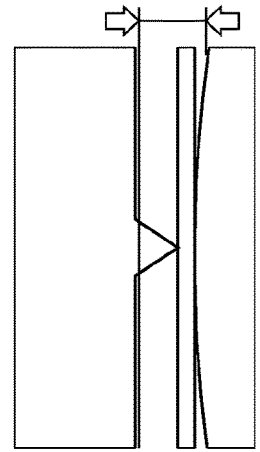

FIGS. 12A-12D show example microstructure patterns, consistent with embodiments of the present disclosure. For example, FIGS. 12A-12D illustrate the optimization of the separation distance between the top and bottom electrodes of the capacitors in zone 2 (capacitors located at the top of the domes). FIG. 12A illustrates a comparison of various sizes of pyramids (from 10 to 50 μm). If the pyramid is smaller, the separation distance between the top and bottom electrodes is smaller. According to equation 1, it results in a larger value of the capacitance $C_{min}$, which directly (positively) impacts the signal-to-noise ratio. FIGS. 12B-12D illustrate a comparison of various separation distances between the pyramids (ratios b/a from 0.4 to 4), and how it influences the value of $C_{min}$. More and smaller pyramids result in higher $C_{min}$. The CNTs conducting layer is marked in a solid black line. The equivalent separation distance between the bottom and top electrodes is marked by the arrows. It is calculated as the average distance between the top and the bottom electrode, taking into account the 3D geometry of both electrodes. Higher Gun, and therefore better SNR are achieved with a smaller separation distance between the pyramids, which corresponds to a smaller equivalent separation distance. In both figures the conditions resulting in the highest $C_{min}$ are marked with a circle.

Figure 13A:
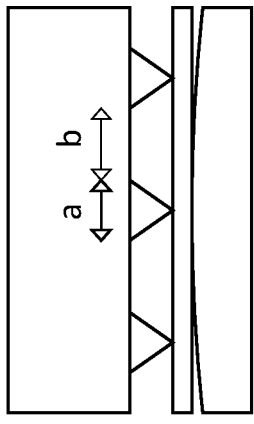
FIGS. 13A-13C show further example microstructure patterns, consistent with embodiments of the present disclosure.
Figure 13A:
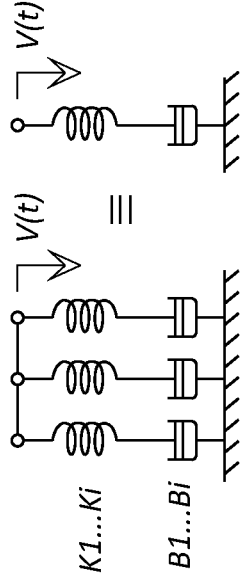
Figure 13B:
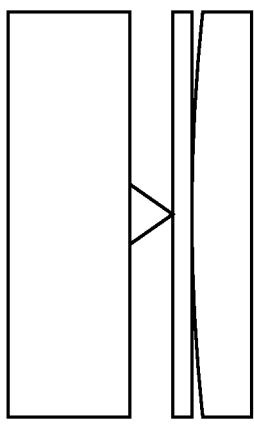
Figure 13B:
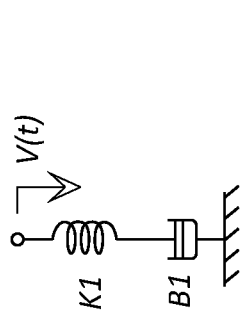
Figure 13C:
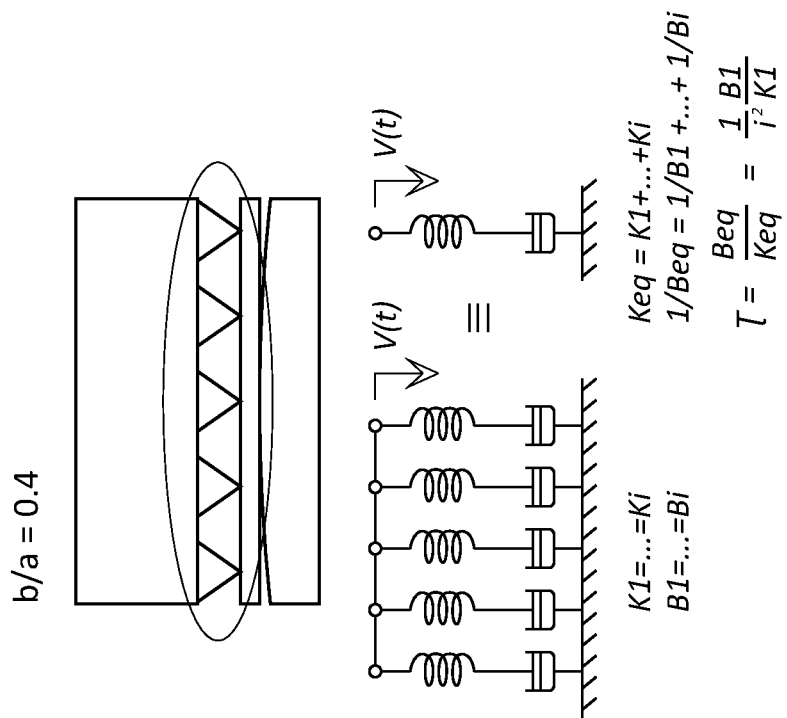

FIGS. 13A-13C show example microstructure patterns, consistent with embodiments of the present disclosure. For example, FIGS. 13A-13C illustrate the optimization of the time-response (zone 2, capacitors located at the top of the domes/hills) by changing the separation distance between pyramids. For example, FIG. 13A illustrates a separation distance between the pyramids ranging from b/a of 4, FIG. 13B illustrates a separation distance b/a of 1.2, and FIG. 13C illustrates a separation distance b/a of 0.4. For each condition, a cross-sectional view showing the pyramids and the equivalent mechanical circuit model are provided. When pressure is applied on the sensor, the pyramids deform reversibly. Each pyramid can be modeled as a spring (constant K) in series with a damper (constant B). The equivalent circuit for several pyramids in parallel and the corresponding system time constant τ are calculated for each condition, indicating that shorter time-response is achieved with b/a=0.4 (best-case scenario, indicated with a circle).

Specific sensor apparatuses in accordance with the present disclosure can measure and distinguish combined normal and shear pressure during different object manipulation as applying different normal pressure and shear pressure. The sensor responds to normal pressure as impedance changes in all and the average impedance is used to analyze the normal pressure. On the other hand, the sensor responds to shear pressure, even with normal pressure, as differences in impedance s that increase in two electrodes while impedance s decrease in others, so the subtraction of the impedance is used to analyze the shear pressure. The demonstration illustrated tactile sensing capabilities of the device, which allows the robotic device to interact with deformable, even stretchable, and fragile objects by manipulating tofu and/or a berry.

Various embodiments are implemented in accordance with the underlying Provisional Application (Ser. No. 62/750,951), entitled "Skin-Like Sensor for Normal and Shear Stress Detection," filed Oct. 26, 2018, to which benefit is claimed and which are both fully incorporated herein by reference for their general and specific teachings. For instance, embodiments herein and/or in the Provisional Application be combined in varying degrees (including wholly). Reference may also be made to the experimental teachings and underlying references provided in the underlying provisional application. Embodiments discussed in the Provisional Application are not intended, in any way, to be limiting to the overall technical disclosure, or to any part of the claimed disclosure unless specifically noted. The Provisional Application illustrates a general sensor apparatus, and specific implementations of the first and second substrates including patterns of microstructures, and experimental embodiments used to optimize the same. It is recognized that the various figures and descriptions herein can be used in combination with a variety of different structures and technical applications as described in the above-referenced Provisional Application, which is fully incorporated herein by reference for all it contains.

Terms to exemplify orientation, such as top view/side view, before or after, upper/lower, left/right, top/bottom, and above/below, may be used herein to refer to relative positions of elements as shown in the figures. It should be understood that the terminology is used for notational convenience only and that in actual use the disclosed structures may be oriented differently than the orientation shown in the figures. Thus, the terms should not be construed in a limiting manner.

As examples, the Specification describes and/or illustrates aspects useful for implementing the claimed disclosure by way of various circuits or circuitry which may be illustrated as or using terms such as blocks, modules, device, system, unit, controller, and/or other circuit-type depictions. Such circuits or circuitry are used together with other elements (robotics, electronic devices, prosthetics, processing circuitry and the like) to exemplify how certain embodiments may be carried out in the form or structures, steps, functions, operations, activities, etc. For example, in certain of the above-discussed embodiments, one or more illustrated items in this context represent circuits (e.g., discrete logic circuitry or (semi)-programmable circuits) for implementing these operations/activities, as may be carried out in the approaches shown in the figures. In certain embodiments, such illustrated items represent one or more circuitry and/or processing circuitry (e.g., microcomputer or other CPU) which is understood to include memory circuitry that stores code (program to be executed as a set/sets of instructions) for performing a basic algorithm (e.g., inputting, counting signals having certain signal strength or amplitude, classifying the type of force including a magnitude and direction using impedance values output by the sensor circuitry, sampling), and/or involving sliding window averaging, and/or a more complex process/algorithm as would be appreciated from known literature describing such specific-parameter sensing. Such processes/algorithms would be specifically implemented to perform the related steps, functions, operations, activities, as appropriate for the specific application.

Based upon the above discussion and illustrations, those skilled in the art will readily recognize that various modifications and changes may be made to the various embodiments without strictly following the exemplary embodiments and applications illustrated and described herein. For example, methods as exemplified in the Figures may involve steps carried out in various orders, with one or more aspects of the embodiments herein retained, or may involve fewer or more steps. Such modifications do not depart from the scope of various aspects of the disclosure, including aspects set forth in the claims.

What is claimed:

1. A sensor apparatus, comprising:
   a plurality of capacitors including:
   a first substrate having a plurality of first electrodes;
   a second substrate having a second electrode; and
   a dielectric material, the plurality of first electrodes and the second electrode being separated by the dielectric material and the plurality of first electrodes are aligned with respect to the second electrode such that each of plurality of first electrodes form one of the plurality of capacitors with the second electrode; and
   sensor circuitry coupled to the plurality of capacitors and to differentiate between normal and shear forces applied to the apparatus based on spatial signal processing of impedance responses of each of the plurality of capacitors formed by the second electrode and the plurality of first electrodes, wherein the spatial signal processing involves use of a sensor field grid, and the sensor circuitry is to differentiate between a normal-directed force and at least one of a shear force and a tilt force by mapping, or using an impedance map having a grid of locations that is indicative of a pattern of impedance responses of an electrode pair and comparing the impedance map to predetermined patterns.

2. The apparatus of claim 1, wherein the plurality of first electrodes include pyramid-shaped microstructures and the second electrode includes a dome-shaped microstructure, and the pyramid-shaped microstructures are positioned orthogonally to the dome-shaped microstructure.

3. The apparatus of claim 1, wherein the plurality of first electrodes include pyramid-shaped microstructures and the second electrode includes a dome-shaped microstructure, and the pyramid-shaped microstructures are positioned in a spiral pattern with respect to the dome-shaped microstructure.

4. The apparatus of claim 1, wherein at least one of the first substrate and the second substrate is formed of an elastomer material and carbon nanotubes.

5. The apparatus of claim 1, wherein the spatial signal processing involves use of a sensor field grid.

6. A sensor apparatus, comprising:
   a plurality of capacitors including:
   a first substrate having a plurality of first electrodes including three-dimensional microstructures embedded on the first substrate;
   a second substrate having a second electrode including a three-dimensional microstructure embedded on the second substrate; and
   a dielectric material, the plurality of first electrodes and the second electrode being separated by the dielectric material and the plurality of first electrodes are aligned with respect to the second electrode such that each of plurality of first electrodes form one of the plurality of capacitors with the second electrode; and
   sensor circuitry coupled to the plurality of capacitors and to differentiate between normal and shear forces applied to the apparatus based on spatial signal processing of impedance responses of each of the plurality of capacitors formed by the second electrode and the plurality of first electrodes, wherein the spatial signal processing involves use of an impedance map including grid locations that indicate impedance responses of one or more respective electrode pairs.

7. The sensor apparatus of claim 6,
   wherein the second substrate includes a plurality of second electrodes, among which is the second electrode, arranged in a pattern, and
   for each of the plurality of second electrodes, a respective subset of the plurality of first electrodes is positioned to align with the respective one of the plurality of second electrodes such that the plurality of first electrodes and plurality of second electrodes form a plurality of arrays of capacitors.

8. A sensor apparatus, comprising:
   a first substrate having a plurality of first microstructures of a first type of shape;
   a second substrate having a plurality of second microstructures of a different second type of shape; and
   a dielectric material between the first and second substrates, wherein each of the plurality of second microstructures aligns with a subset of the first microstructures, thereby forming a plurality of arrays of capacitors,
wherein each subset of the first microstructures is arranged with respect to a second microstructure from among the second microstructures such that a first microstructure of the subset from among the first microstructures is arranged with respect to a top of the second microstructure, and certain of the first microstructures are arranged with respect to one or more slopes of the second microstructure.

9. The apparatus of claim 8, further including sensor circuitry coupled to the plurality of arrays of capacitors and configured and arranged to measure and differentiate between normal and shear forces applied to the sensor apparatus based on a pattern of impedance responses of each of the plurality of arrays of capacitors.

10. The apparatus of claim 8, wherein the plurality of first microstructures include electrodes and the plurality of second microstructures include electrodes, and each array of capacitors includes a plurality of electrode pairs formed by the second microstructure and the respective subset of the first microstructures.

11. The apparatus of claim 8, wherein each subset of the plurality of first microstructures is arranged in a phyllotaxis spiral with respect to with one of the plurality of second microstructures.

12. The apparatus of claim 8, wherein the first and second substrates include an elastomer, and the plurality of first microstructures and second microstructures include carbon nanotube material and the elastomer.

13. The apparatus of claim 12, wherein the elastomer is to elastically deform in response to pressure applied, and to store and release energy reversibly.

14. The apparatus of claim 8, wherein at least some of the plurality of first microstructures include pyramid-shaped microstructures, and are arranged in a grid pattern on the first substrate with a distance between of b and having a length of a, wherein the ratio of b/a is from 0.4-4.0.

15. The apparatus of claim 8, wherein each subset of the first microstructures is arranged with respect to the respective second microstructure such that the first microstructure is arranged with respect to a top of the second microstructure, four of the first microstructures of the subset are arranged with respect to slopes of the second microstructure, four of the first microstructures of the subset are arranged with respect to corners of the second microstructure, and sixteen of the first microstructures are arranged surrounding the second microstructures.

16. A method comprising:
forming a first substrate of elastomer having a plurality of pyramid-shaped microstructures embedded thereon;
forming a second substrate of the elastomer having a plurality of dome-shaped microstructures embedded thereon; and
combining the first substrate and the second substrate, with a dielectric material between, such that each one of the plurality of dome-shaped microstructures is aligned with a different subset of plurality of the pyramid-shaped microstructures, and the plurality of pyramid-shaped microstructures and dome-shaped microstructures form a plurality of arrays of capacitors, wherein at least one of the forming steps includes patterning a wafer with a carbon-nanotube coating or layer, and releasing an elastomer substrate from the wafer to form one of the first substrate and the second substrate.

17. The method of claim 16, further including laminating the first substrate, the dielectric material and the second substrate.

18. The method of claim 16, wherein forming the first substrate further includes patterning the wafer for forming pyramid shapes;
coating the wafer with a carbon-nanotube layer;
forming an elastomer substrate on the wafer with the carbon-nanotube layer; and
releasing the elastomer substrate from the wafer to form the first substrate having the plurality of pyramid-shaped microstructures embedded thereon.

19. The method of claim 16, wherein forming the second substrate further includes:
patterning the wafer, wherein the wafer includes silicon;
coating the wafer with a carbon-nanotube layer;
forming an elastomer substrate on the wafer with the carbon-nanotube layer;
releasing the elastomer substrate from the wafer to form the second substrate; and
applying a vacuum to the second substrate to form the plurality of dome-shaped microstructures embedded thereon.

* * * * *